US008410078B2

(12) United States Patent
Liang et al.

(10) Patent No.: US 8,410,078 B2
(45) Date of Patent: Apr. 2, 2013

(54) COMPOSITION AND METHODS TO TREAT CARDIAC DISEASES

(75) Inventors: Bruce Tsan Liang, Avon, CT (US); Achilles Pappano, West Simsbury, CT (US); Jian-Bing Shen, Farmington, CT (US)

(73) Assignee: University of Connecticut, Farmington, CT (US)

( * ) Notice: Subject to any disclaimer, the term of this patent is extended or adjusted under 35 U.S.C. 154(b) by 1333 days.

(21) Appl. No.: 11/751,699

(22) Filed: May 22, 2007

(65) Prior Publication Data

US 2007/0281908 A1    Dec. 6, 2007

Related U.S. Application Data

(60) Provisional application No. 60/802,878, filed on May 23, 2006, provisional application No. 60/893,946, filed on Mar. 9, 2007.

(51) Int. Cl.
*A61K 31/675* (2006.01)
*A61K 31/52* (2006.01)
*A61K 31/517* (2006.01)
*C07F 9/02* (2006.01)

(52) U.S. Cl. ....... 514/81; 514/263.4; 514/269; 544/244; 544/277

(58) Field of Classification Search .................... 514/81, 514/269, 263.4, 263.3; 544/244, 277
See application file for complete search history.

(56) References Cited

U.S. PATENT DOCUMENTS

| 6,255,292 | B1 | 7/2001 | Liang |
| 6,329,349 | B1 | 12/2001 | Liang et al. |
| 6,586,413 | B2 | 7/2003 | Liang et al. |
| 6,677,356 | B1 * | 1/2004 | Sethi et al. ..................... 514/321 |
| 7,087,589 | B2 | 8/2006 | Jacobson et al. |
| 2003/0092668 | A1 | 5/2003 | Liang et al. |
| 2003/0186929 | A1 | 10/2003 | Liang et al. |
| 2003/0216412 | A1 | 11/2003 | Jacobson et al. |

FOREIGN PATENT DOCUMENTS

| WO | 0151490 A1 | 7/2001 |
| WO | 2006031505 A1 | 3/2006 |

OTHER PUBLICATIONS

Saks et al. J. Molecular and Cellular Cardiology 21(10) (1998) Abstract only.*
Dhalla et al. J. Molecular and Cellular Cardiology 20 (20) (1988) Abstract only.*
Lambrecht et al. Current Pharmaceutical Design (2002), 8, 2371-2399.*
Gao et al Am J Physiol Heart Circ Physiol 288:H2238-H2243, 2005).*
Ravi et al., "Adenine Nucleotide Analogues Locked in a Northern Methanocarba Conformation: Enhanced Stability and Potency as P2Y1 Receptor Agonists", Journal of Medicinal Chemistry, vol. 45, No. 10, 2002, pp. 2090-2100.
Kim et al., "2-Substitution of Adenine Nucleotide Analogues Containing a Bicyclo[3.1.0]hexane Ring System Locked in a Northern Conformation: Enhanced Potency as P2Y1 Receptor Antagonists" Journal of Medicinal Chemistry, vol. 46, No. 23, 2003, pp. 4974-4987.
Hu, Bing et al; "A Novel Contractile Phenotype with Cardiac Transgenic Expression of the Human P2X4 Receptor"; The FASEB Journal; 15; pp. 2739-2741; (2001).
Knollmann, Bjorn C. et al; "Remodelling of Ionic Currents in Hypertrophied and Failing Hearts of Transgenic Mice Overexpressing Calsequestrin"; Journal of Physiology; 525; pp. 483-498; (2000).
Mei, Qibing et al; "P2 Purinergic Receptor Activation Enhances Cardiac Contractility in Isolated Rat and Mouse Hearts"; Am. J. Physiol Heart Circ. Physiol.; 281; pp. H334-H341; (2001).
North, R. Alan; "Molecular Physiology of P2X Receptors"; Physiol. Rev.; 82; pp. 1013-1067; (2002).
Parker, Karen E. et al; "An ATP-Activated Nonselective Cation Channel in Guinea Pig Ventricular Myocytes"; American Journal of Physiology; 269; pp. H789-H797; (1995).
Scamps, Frederique et al; "Pharmacological Profile of the ATP-Mediated Increase in L-Type Calcium Current Amplitude and Activation of a Non-Specific Cationic Current in Rat Ventricular Cells"; Br. J. Pharmacol.; 113; pp. 982-986; (1994).
Shen, Jian-Bing et al; "Extracellular ATP-Stimulated Current in Wild-Type and P2X4 Receptor Transgenic Mouse Ventricular Myocytes: Implications for a Cardiac Physiologic Role of P2X4 Receptors"; The FASEB Journal; 20; pp. 277-282; (2006).
Shen, Jian-Bing et al; "P2X Purinergic Receptor-Mediated Ionic Current in Cardiac Myocytes of Calsequestrin Model of Cardiomyopathy: Implications for the Treatment of Heart Failure"; Am. J. Physiol. Heart Circ. Physiol.; 292; pp. H1077-H1084; (2007).
Terracciano, C.M.N. et al; "Clinical Recovery From End-Stage Heart Failure Using Left-Ventricular Assist Device and Pharmacological Therapy Correlates With Increased Sarcoplasmic Reticulum Calcium Content but Not With Regression of Cellular Hypertrophy"; Circulation; 109; pp. 2263-2265; (2004).
Xu, Hao et al; "Characterization of a Stimulatory Adenosine A2a Receptor in Adult Rat Ventricular Myocyte"; American J. Physiol.; 270; pp. H1655-H1661; (1996).
Yang, Alexander et al; "A Beneficial Role of Cardiac p2X4 Receptors in Heart Failure: Rescue of the Calsequestrin Overexpression Model of Cardiomyopathy"; Am. J. Physio. Heart Circ. Physiol.; 287; pp. H1096-H1103; (2004).
Hiroke, et al; "ATP Induces Cardiomyocyte Hypertrophy Through the Calcineurin Dependent Ca2+ Signaling Pathway"; Circulation; 100; p. I. 628; (1999); XP008085345.

(Continued)

*Primary Examiner* — Shirley V Gembeh
(74) *Attorney, Agent, or Firm* — Cantor Colburn LLP

(57) ABSTRACT

Disclosed herein are N-methanocarba derivatives of AMP and their use in the treatment of cardiac and vascular diseases and conditions responsive to activation of the cardiac P2X receptor. In one embodiment, the N-methanocarba derivative of AMP is the N-methanocarba derivative of 2-chloro-AMP. Diseases and conditions responsive to activation of the cardiac P2X receptor include, for example, cardiac hypertrophy, cardiac failure resulting from any cause of abnormal $Ca^{2+}$ homeostasis or from myocardial injuries, vascular insufficiency leading to myocardial infarction, post-myocardial infarction conditions, post-myocardial infarction conditions within the short-term post-infarction period, and diastolic heart failure.

14 Claims, 15 Drawing Sheets

OTHER PUBLICATIONS

Mahaut-Smith, et al; "ADP Is Not an Agonist at P2X(1) Receptors: Evidence for Separate Receptors Stimulated by ATP and ADP on Human Platelets"; British Journal of Pharmacology; 131; pp. 108-114; (2000); XP008085367.

International Search Report and Written Opinion of the International Searching Authority; International Application No. PCT/US2007/012151; International Filing Date May 22, 2007; Applicant's File Reference UCT-0118; Date of Mailing Nov. 7, 2007; 19 pages.

"2009 Focused Update Incorporated Into the ACC/AHA 2005 Guidelines for the Diagnosis and Management of Heart Failure in Adults"; J. Am. Coll. Cardiol.; Published on-line, 92 pages; Mar. 26, 2009.

Komamura, et al.; "Alterations in Left Ventricular Diastolic Function in Conscious Dogs with Pacing-Induced Heart Failure"; J. Clin. Invest; 89; pp. 1825-1838; (1992).

Janardhanan, et al.; "Therapeutic Approach to Diastolic Dysfunction"; Current Hypertens. Rep.; 11(4); pp. 283-291; (2009).

Liu; "A New Epidemic of Heart Failure in the United States: Findings from the National Hospital Discharge Surveys, 1980-2006"; Circ. 18; S1092; Abstract only, 2 pages (2008).

Ohara, et al.; "Evolving Focus on Diastolic Dysfunction in Patients with Coronary Artery Disease"; Curr. Opin. Cardiol.; 25; pp. 613-621; (2010).

Opie, et al.; "Controversies in Ventricular Remodeling"; Lancet; 367; pp. 356-367; (2006).

O'Rourke, et al.; "Mechanisms of Altered Excitation-Contraction Coupling in Canine Tachycardia-Induced Heart Failure, I: Experimental Studies"; Circ. Res.; 84; pp. 562-570; (1999).

Shannon, et al.; "Effects of Renin Inhibition Compared to Angiotensin Converting Enzyme Inhibition in Conscious Dogs with Pacing-Induced Heart Failure"; Cardiovascular Research; 34; pp. 464-472; (1997).

Tenenbaum, et al.; "Toward a Redefinition of Ischemic Cardiomyopathy: Is It an Indivisible Entity?"; J. Am. Coll. Cardiol.; 40; pp. 205-206; (2002).

Ukai, et al.; "Allopurinol Enhances the Contractile Response to Dobutamine and Exercise in Dogs with Pacing-Induced Heart Failure"; Circulation; 103; pp. 750-755; (2001).

Liu, Longjian; "Changes in Cardiovascular Hospitalization and Comorbidity of Heart Failure in the United States: Findings from the National Hospital Discharge Surveys 1980-2006"; International Journal of Cardiology xxx (2010) Article in Press; IJCA-12412; 7 pages.

Burnstock, Geoffrey; "Introduction: P2 receptors"; Current Topics in Medicinal Chemistry; 4; pp. 793-803; (2004).

Zhou, et al.; "Treatment of Heart Failure by a Methanocarba Derivative of Adenosine Monophosphate: Implication for a Role of Cardiac Purinergic P2X Receptors"; Journal of Pharmacology and Experimental Therapeutics; 333; pp. 920-928; (2010).

Sonin, et al.; "Role of P2X Purinergic Receptors in the Rescue of Ischemic Heart Failure"; Am. J. Physiol Heart Circ Physiol; 295; pp. H1191-H1197; (2008).

Shen, et al.; "P2X Purinergic Receptor-Mediated Ionic Current in Cardiac Myocytes of Calsequestrin Model of Cardiomyopathy: Implications for the Treatment of Heart Failure"; Am J Physiol Heart Circ Physiol; 292; pp. H1077-H1084; (2006).

Brown, et al.; "Activity of Novel Adenine Nucleotide Derivatives as Agonists and Antagonists at Recombinant Rat P2X Receptors"; Drug Development Research; 49; pp. 253-259; (2000).

* cited by examiner

MRS2339 can increase +dP/dt of intact CSQ mouse hearts

MRS2339 Increased +dP/dt in WT mouse hearts

The beta blocker metoprolol further enhanced survival of $P2X_4R$/CSQ binary mice

COMPOSITION AND METHODS TO TREAT CARDIAC DISEASES

CROSS-REFERENCE TO RELATED APPLICATIONS

This application claims the benefit of U.S. Patent Application Ser. Nos. 60/802,878 filed May 23, 2006 and 60/893,946 filed on Mar. 9, 2007, which are incorporated by reference herein in their entirety.

STATEMENT REGARDING FEDERALLY SPONSORED RESEARCH & DEVELOPMENT

The U.S. Government has certain rights in this invention pursuant to National Institutes of Health Grant No. RO1-HL48225.

BACKGROUND

Receptors for purine nucleotides, known as P2 purinergic receptors, mediate a number of potent and possibly important biological effects in the cardiovascular system. The P2X ion channels are receptor channels activated by extracellular ATP, while the P2Y receptors are G protein-coupled receptors. Together, they represent two sub-families of the P2 nucleotide receptors. Previous studies have shown that extracellular ATP can cause an ionic current in murine, rat and guinea pig cardiac ventricular myocytes. The receptor that mediates this current appears to be a P2X receptor, of which the $P2X_4$ receptor is an important subunit. Activation of P2X receptors leads to the opening of a nonselective cation channel permeable to $Na^+$, $K^+$ and $Ca^{2+}$. The current is inward at negative membrane potentials, reverses near 0 mV, and becomes outward at positive potentials. The continuous activation of this receptor channel by endogenous extracellular ATP may assume an important biological function. This constant activation under the resting or negative membrane potentials would produce an inward current, while its activation during depolarized portions of the action potential should lead to an outward current. These currents represent a possible ionic mechanism by which the cardiac P2X channel achieves its biological effects.

While activation of P2X receptors is known to mediate ion currents, little is known about the biological role of this ion current mediation. In addition, the effect of P2X receptor agonists on biological functions of P2X including cardiac function and contractility is not understood. There remains a need for the elucidation of the role of P2X receptors and their agonists on cardiac function and contractility.

SUMMARY

In one embodiment, a method of treating a mammalian subject in need of treatment for a cardiac or vascular disease or condition responsive to activation of the cardiac P2X receptor comprises administering an effective amount of an N-methanocarba derivative of AMP for the treatment for the cardiac or vascular disease or condition responsive to activation of the cardiac P2X receptor.

In another embodiment, a method of improving cardiac contractile performance in a mammal in need thereof comprises administering an effective amount of an N-methanocarba derivative of AMP for the treatment for the improvement of cardiac contractile performance.

In yet another embodiment, method of treating a mammalian subject in need of treatment for a cardiac hypertrophy comprises administering an effective amount of a cardiac P2X receptor agonist.

Figure 1:
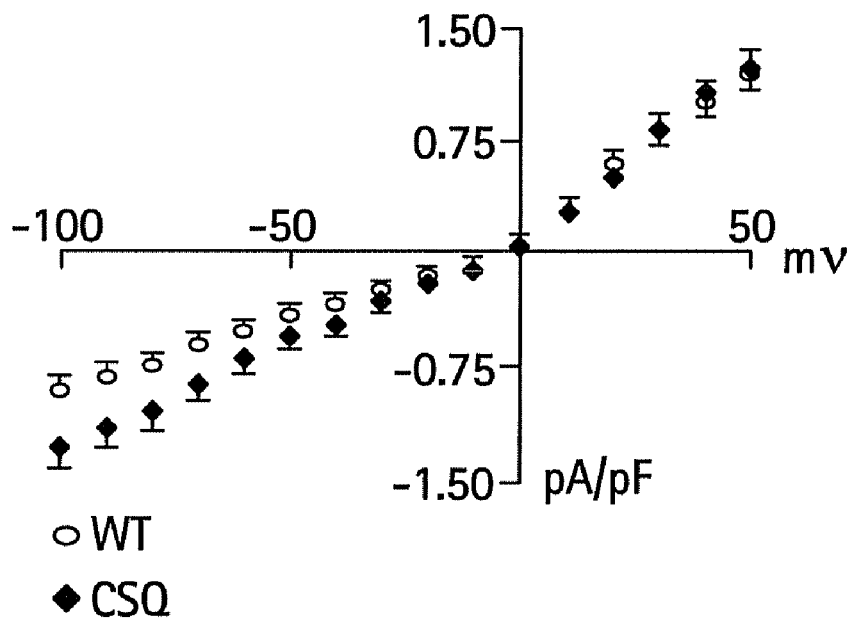
FIG. 1 shows the characterization of 2-meSATP-stimulated current in both WT and CSQ ventricular myocytes measured by voltage clamp in the whole cell configuration. 2-meSATP (3 µM) induced a steady inward current at negative potentials and an outward current at positive potentials with reverse potential near 0 mV.

The above-described and other features will be appreciated and understood by those skilled in the art from the following detailed description and appended claims.

DETAILED DESCRIPTION

The present invention includes nucleotidase-resistant P2X receptor agonists, specifically N-methanocarba derivatives of AMP, and methods of using the agonists. It has been unexpectedly discovered by the inventors herein that N-methanocarba derivatives of AMP are agonists of P2X receptors, and not P2Y receptors as previously believed. Included herein is the use of N-methanocarba derivatives of AMP such as MRS2339 in the treatment of cardiac and vascular diseases and conditions responsive to activation of the cardiac P2X receptor. Cardiac and vascular diseases and conditions responsive to activation of the cardiac P2X receptors include cardiomyopathy and those diseases associated with defects in cardiac contractility. As agonists of P2X receptors, the N-methanocarba derivatives of AMP are particularly useful in the treatment of cardiac hypertrophy, cardiac failure resulting from any cause of abnormal Ca$^{2+}$ homeostasis or from myocardial injuries, vascular insufficiency leading to myocardial infarction, for post-myocardial infarction conditions, for post-myocardial infarction conditions within the short-term post-infarction period, and for diastolic heart failure.

One object of the present invention is to elucidate the regulation of the cardiac P2X receptor in cardiac hypertrophy and/or failure. For example, it is not clear from previous studies whether an increased activation of the endogenous P2X receptor channel is beneficial or harmful in the progression of heart failure. The inventors herein have investigated the regulation of the P2X receptor-mediated ionic current and its potential role in heart failure using the well-established calsequestrin (CSQ) model of cardiomyopathy. It was unexpectedly discovered that chronic administration of N-methanocarba derivatives of AMP reduced cardiac hypertrophy and increased lifespan. Advantageously, the N-methanocarba derivatives of AMP are capable of inducing this ionic current and devoid of any vasodilator action. In one embodiment, the present invention is directed to N-methanocarba derivatives of AMP and their use to treat cardiac disease such as cardiac hypertrophy and/or cardiac failure resulting from abnormal Ca$^{2+}$ homeostasis. Cardiac failures resulting from abnormal Ca$^{2+}$ homeostasis include, for example, drug-induced cardiac failure, toxin-induced cardiac failure, alcohol-induced cardiac failure, cardiac failure due to congenital heart disease, or cardiac failure due to valvular disease.

Another object of the present invention is to elucidate the mechanism of P2X receptor-mediated enhancement of contractility and to define the role of this receptor in heart failure progression after left anterior descending coronary (LAD) ligation-induced infarction. Transgenic mice with cardiac-restricted overexpression of the P2X$_4$ receptor (P2X$_4$R Tg) were used as a model. Activation of the cardiac P2X receptor led to an enhanced myocyte contraction shortening and calcium transients in association with an increased sarcoplasmic reticulum (SR) calcium store. These increases occurred in the absence of any change in the sensitivity to intracellular calcium or the activity of L-type calcium channels. The P2X$_4$R Tg animals survived better than the non-transgenic animals following LAD ligation-induced myocardial infarction and showed an enhanced cardiac performance at 7 days and 2 months after infarct. It was thus unexpectedly discovered that a P2X receptor receptor-induced pathway increases contractile performance and confers a salutary effect in ischemic cardiomyopathy after infarction. It was also unexpectedly discovered that N-methanocarba derivatives of AMP enhance survival after myocardial infarction. In another embodiment, the present invention includes N-methanocarba derivatives of AMP and their use to treat post-myocardial infarction, particularly within the short-term post-infarction period.

In one embodiment, the nucleotidase-resistant P2X receptor agonist is an N-methanocarba derivative of AMP. Structurally constraining the methanocarba ring in the (N) conformation confers relative resistance to 5'-nucleotidase-mediated hydrolysis of AMP analogs. The rate of hydrolysis by rat 5'-ectonucleotidase of (N) methanocarba AMP, for example, was only 0.14% of the rate of hydrolysis of AMP. Suitable N-methanocarba derivatives of AMP are described in U.S. Patent Publication 2003/0216412, incorporated herein by reference.

Suitable N-methanocarba derivatives of AMP are given in Formula I below:

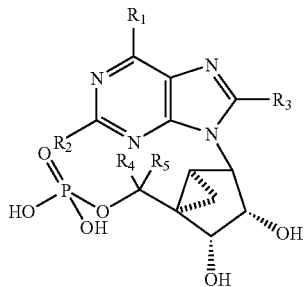

Formula I

The N-methanocarbo derivative may also be a pharmaceutically acceptable salt of Formula I. Within Formula I the variables $R_1$-$R_5$ carry the following definitions:

$R_1$ is hydrogen, alkyl, alkoxy, amino, mono- or di-alkylamino, mono or bicyclic cycloalkyl, cycloalkyloxy, aryl, arylalkyl, acyl, sulfonyl, arylsulfonyl, or a mono- or bicyclic thiazolyl group.

$R_2$ is hydrogen, halogen, thiol, cyano, alkyl, alkenyl, alkynyl, alkylthio, alkylsulfinyl, alkylsulfonyl, aryl, arylamino, or aryloxy.

$R_3$ is hydrogen, halogen, methyl, or ethyl.

$R_4$ and $R_5$ are independently hydrogen, methyl, or methoxy.

Within certain embodiments the N-methanocarba derivative is a compound of Formula I and the variables $R_1$-$R_5$ are defined as follows:

$R_1$ is hydrogen, $C_1$-$C_4$alkyl, $C_1$-$C_4$alkoxy, amino, mono- or di-$C_1$-$C_4$alkylamino, $C_3$-$C_7$cycloalkyl, or $C_3$-$C_7$cycloalkyloxy.

$R_2$ is hydrogen, halogen, thiol, cyano, $C_1$-$C_4$alkyl, $C_1$-$C_4$alkylthio, $C_1$-$C_4$alkylsulfinyl, or $C_1$-$C_4$alkylsulfonyl.

$R_3$, $R_4$, and $R_5$ are all hydrogen.

In a specific embodiment, the nucleotidase-resistant P2X receptor agonist is the N-methanocarba derivative of 2-chloro-AMP (MRS2339), Formula II below:

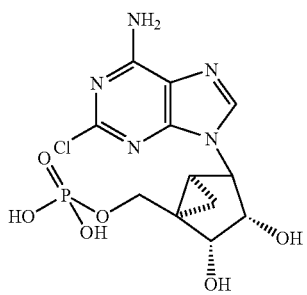

Formula II

Methods in which the nucleotidase-resistant P2X receptor agonist is a pharmaceutically acceptable salt of Formula II are also included.

The N-methanocarba derivatives of AMP in accordance with formula I have an affinity for P2X receptors. The P2X receptor affinity of the N-methanocarba derivatives of AMP can be determined by the dose-response of increases in contractility for the different compounds. Changes in contractility can be measured as changes in sarcomere length and $Ca^{2+}$ transients recorded from single isolated myocytes using an epi-fluorescence inverted microscope.

In one embodiment, the N-methanocarba derivatives of AMP are useful in the treatment of cardiac diseases responsive to activation of the cardiac P2X receptor such as, for example, cardiac hypertrophy and/or cardiac failure resulting from abnormal $Ca^{2+}$ homeostasis. Previous data suggested that an increased expression or activation of the cardiac P2X receptor may exert a salutary role in cardiac hypertrophy and failure. In order to elucidate the regulation of cardiac P2X current in failing cardiac myocytes and the effect of nucleotidase-resistant P2 receptor agonists on the cardiac P2X current, the CSQ model of hypertrophy and severe heart failure was employed. CSQ mice are a model of severe heart failure that is caused by overexpression of the sarcoplasmic reticulum $Ca^{2+}$ binding protein calsequestrin. The CSQ mouse model is characterized by aggressive dilated cardiomyopathy followed by premature death at 16 weeks of age. CSQ transgenic mice exhibit many of the features of human cardiomyopathy, including cardiac enlargement, depressed contractile function, and abnormal β-adrenergic receptor signaling. CSQ mice are thus an accepted model system in which to study the pathogenesis and progression of cardiac hypertrophy and heart failure resulting from abnormal $Ca^{2+}$ homeostasis.

The effects of a known P2X agonist in CSQ mice were studied to determine if a P2X agonist could affect membrane currents in ventricular myocytes. The P2X agonist, 2-methylthio adenosine triphosphate (2-meSATP), induced a membrane current in ventricular myocytes isolated from both wild type mice and CSQ mice. The current-voltage (I-V) relationship and the reverse potential were similar in both kinds of cardiac myocytes. However, the density of the 2-meSATP-evoked current was greater in CSQ than in wild type myocytes. Although the CSQ myocytes are hypertrophic and larger, the current was normalized against the larger capacitance of the CSQ myocytes as current density in pA/pF. These data suggest that the P2X current is up-regulated in the cardiac myocytes of the CSQ mice. While it is not known whether the cardiac P2X receptor protein level is increased and accounts for the larger current density in the CSQ myocytes, the level of one of the known subunits, that of the $P2X_4$ receptor, was increased in these myocytes. Since the exact identity of the other P2X subunits of this native cardiac P2X receptor is not known, the level of these other subunits may also be up-regulated in the failing CSQ hearts. Nevertheless, the larger current density mediated via the endogenous P2X receptor and higher levels of its P2X4 subunit suggest an upregulation of this receptor in the failing cardiac myocyte.

Further characterization of the 2-meSATP-evoked current in the wild type murine cardiac myocyte demonstrated a lack of inhibition of the 2-meSATP current by guanosine-5'-O-(2-thiodiphosphate) (GDPβS) that was present at a concentration known to block GDP/GTP exchange, suggesting against a role of the G protein in mediating this current. This finding, along with the observations that the P2Y agonist 2-meSADP could not evoke any current and that $P2Y_1$ selective antagonist MRS2500 ((1'R,2'S,4'S,5'S)-4-(2-iodo-6-methylamino-purin-9-yl)-1-[(phosphate)-methyl]-2-(phosphate)-bicyclo [3.1.0]hexane) could not block the current induced by either 2-meSATP or MRS2339, strongly suggest against a role of the G protein-coupled P2Y receptor in the induction of this current. Three additional P2X receptor-selective antagonists were used. NF449 (4,4',4'',4'''-(carbonylbis(imino-5,1,3-benzenetriylbis(carbonylimino)))tetrakis-benzene-1,3-disulfonic acid) is selective for native rat $P2X_1$ receptors vs. native guinea pig $P2X_3$ and $P2Y_1$ receptors, or vs. native human $P2Y_2$ receptors in HEK293 cells. NF449 is also selective for recombinant human $P2X_1$ vs. $P2X_7$ receptors expressed in the *Xenopus oocytes*. Although the selectivity of NF449 for native murine P2 receptors is not known, one may infer from the data using NF449 that homomeric $P2X_1$ receptor is unlikely part of the native cardiac P2 receptor mediating the 2-meSATP-induced current. At 5 μM, pyridoxal-phosphate-6-azophenyl-2',4'-disulphonic acid (BBG) can block the rat and human $P2X_7$ receptor but will not block rat $P2X_3$, $P2X_{2/3}$, $P2X_4$, or $P2X_{1/5}$ receptors. It may partially inhibit the rat $P2X_2$ or the human $P2X_4$ receptor. At this concentration, BBG can nearly abrogate human $P2X_5$ receptor-mediated current. Since there is no data regarding the effect of BBG on any of the murine P2X receptors, one cannot definitively exclude a role of homomeric $P2X_5$ and $P2X_7$ receptors in mediating the 2-meSATP current in the murine myocyte. That P2X receptor antagonists (PPADS) can block most of the 2-meSATP-evoked current is consistent with a role of the $P2X_4$ receptor as a subunit of the native P2X receptor that mediates this current. This conclusion is also consistent with our previous findings that showed a partial sensitivity of the current to antagonism by suramin.

In order to investigate the role of the native cardiac P2X receptor in heart failure, MRS2339 was administered to CSQ mice. While the effects described herein have been demonstrated for MRS2339, it is believed that similar effects will be achieved with other P2 receptor agonists, particularly N-methanocarba derivatives of AMP. When administered chronically in vivo to the failing CSQ mice, MRS2339 reduced cardiac hypertrophy, as shown by decreases in myocyte size and heart weight/body weight ratios, and by prolonged survival. Without being held to theory, it is believed that activation of the cardiac P2X receptor is important in the beneficial effect observed with MRS2339. First, the anti-hypertrophic effect of myocyte-specific overexpression of the $P2X_4$ receptor is similar to that of the in vivo administration of MRS2339. The salutary effects of MRS2339 and myocyte-specific overexpression of the $P2X_4R$ in the same animal model of heart failure are nearly identical with reductions in myocyte size and heart weight/body weight ratio as well as prolongation of lifespan. Second, this P2 agonist was capable of inducing a current similar to that evoked by the P2X agonist 2-meSATP in not only the WT but also the CSQ cardiac myocytes. During administration of this 5'-nucleotidase-resistant agonist, the cardiac P2X receptor was likely activated to some degree in vivo. Third, this agonist is devoid of any vasodilator effect at concentration as high as 10 μM, while the vasodilator action of acetylcholine was striking and readily demonstrated in the same vascular ring preparation. The lack of any in vitro vasodilator effect suggests against any vascular unloading as a cause of the beneficial effect of this agonist in heart failure animals. However, since the blood pressure in the CSQ animals is not known, a possible MRS2339-induced decrease in the blood pressure may have contributed to the salutary effect observed.

MRS2339 and the N-methanocarba derivatives of AMP are particularly useful in the treatment of cardiac failure resulting from abnormal $Ca^{2+}$ homeostasis. While the CSQ model is a heart failure model that arises from abnormal calcium handling and homeostasis, abnormal calcium handling plays an important contributing if not a pathogenic role in the development of heart failure. Therefore, the beneficial effect of MRS2339 and other N-methanocarba derivatives of AMP and their evoked currents may be generalized to other models of heart failure. The mechanism by which the cardiac P2X current achieves its salutary effect in heart failure is unknown. The inward current at negative potentials may increase the SR calcium loading and enhance the performance of the failing heart. The outward current at positive potentials may enhance repolarization during phase 1 or 2, and thereby shorten the action potential duration with resultant decreased calcium influx and reduced stimulus for cardiac hypertrophy. The duration of action potential and its manipulation have been implicated in the development or modulation of cardiac hypertrophy.

Overall, the cardiac myocyte P2X receptor is up-regulated in the CSQ model of hypertrophy and heart failure. Chronic in vivo administration of the P2X agonist MRS2339 and other N-methanocarba derivatives of AMP can rescue the hypertrophic phenotype of the CSQ animals and prolong their longevity. This salutary effect appears to be mediated by activation of the up-regulated cardiac P2X receptor. The data imply that augmentation of the cardiac myocyte P2X current can reverse or attenuate cardiac hypertrophy and failure and suggest that agonists at this nucleotide-gated receptor channel represent a new therapeutic target.

In one embodiment, N-methanocarba derivatives of AMP such as MRS2339 are used in the treatment of cardiac diseases responsive to activation of the cardiac P2X receptor such as cardiomyopathy. Cardiac diseases responsive to activation of cardiac P2X include, for example, cardiac hypertrophy and/or cardiac failure resulting from abnormal $Ca^{2+}$ homeostasis. Cardiac hypertrophy is a thickening of the heart muscle (myocardium), which results in a decrease in size of the chamber of the heart, including the left and right ventricles. Alterations in $Ca^{2+}$ handling are known to be associated with cardiac hypertrophy. Cardiac failure is the failure of the heart to maintain a cardiac output sufficient to meet the metabolic demands of the body. Cardiac failure can result from any structural or functional cardiac disorder that impairs the ability of the heart to fill with or pump a sufficient amount of blood throughout the body. N-methanocarba derivatives of AMP such as MRS2339 are particularly useful in the treatment if cardiac failure resulting from abnormal $Ca^{2+}$ homeostasis.

In another embodiment, the mechanism of P2X receptor-mediated enhancement of contractility and the role of this receptor in heart failure progression after left anterior descending coronary (LAD) ligation-induced infarction were studied. Activation of cardiac P2X receptors is capable of enhancing the contractile state of the myocyte and intact heart. Little was known regarding the mechanism of P2X receptor-mediated increase in contractility or the biological function of this receptor. Using transgenic mice with cardiac-specific overexpression of $P2X_4$ receptors as a model, the present data showed that an increased sarcoplasmic reticulum (SR) $Ca^{2+}$ loading is the mechanism of P2X receptor-mediated increase in contractility and that this receptor channel is capable of enhancing survival and improving cardiac performance after myocardial infarction.

Extracellular ATP released from sympathetic nerves, activated platelets, endothelial or cardiac cells can exert a number of cardiovascular effects. These effects are mediated via either the G protein-coupled P2Y receptors or the ligand-gated P2X receptor channels. In the heart, activation of the cardiac myocyte P2X receptor or its overexpression can cause increased contractility. Of the P2X receptor subfamily, the $P2X_4$ receptor is an important subunit of the cardiac myocyte P2X receptor. Cardiac myocytes isolated from transgenic mice with cardiac-specific overexpression of the $P2X_4$ receptor were developed as a model to investigate the mechanism of enhanced contractility. A number of lines of evidence suggest that the mechanism of this enhanced contractile state is the result of an increased SR $Ca^{2+}$ loading via this receptor channel by extracellular ATP. First, activation of the overexpressed P2X$_4$ receptor by the P2X agonist 2-meSATP caused increased intracellular Ca$^{2+}$. This increase in cellular Ca$^{2+}$ transient was temporally associated with the increase in myocyte contractility. Second, activation of the receptor channel in P2X$_4$R transgenic (Tg) myocytes increased the caffeine-induced I$_{Na/Ca}$ inward current in the presence of extracellular 2-meSATP. This increase in I$_{Na/Ca}$ current was not due to an increased I$_{Na/Ca}$ density in the Tg myocyte since the latter has similar basal I$_{Na/Ca}$ density as the nontransgenic (NTG) myocytes. Instead, the increased I$_{Na/Ca}$ current was the result of an increased SR Ca$^{2+}$ store. Third, the relationship between the change in contracile shortening (CS) and that of intracellular Ca$^{2+}$ was the same before and after P2X agonist application. The slopes were virtually identical. These data showed that activation of the overexpressed P2X$_4$ receptor did not change sensitivity to cellular Ca$^{2+}$, suggesting against the possibility that an enhanced Ca$^{2+}$ sensitivity was the mechanism of receptor-induced contractility increase. Fourth, previous study demonstrated that activation of the native or the overexpressed cardiac P2X receptors had no effect on the L-type Ca$^{2+}$ channel current, ruling out an increased L-type channel activity as a cause of the increased myocyte contractility via P2X receptors. Finally, the agonist-induced increase in Tg myocyte contractility was not associated with any cyclic AMP increase, consistent with a lack of effect of P2X receptor activation on the L-type Ca$^{2+}$ channel.

As explained above, there is a beneficial, protective function of the cardiac P2X receptor in the CSQ model of cardiomyopathy and heart failure. Rescue of the CSQ heart failure phenotype by cardiac-specific overexpression of P2X$_4$ receptors may be the result of a P2X receptor-mediated enhanced SR Ca$^{2+}$ store and function. Whether cardiac P2X receptor can also favorably impact heart failure from other etiologies is not known. The present data showed that P2X$_4$R Tg animals have an improved survival after LAD ligation-induced myocardial infarction. All deaths occurred within 7-8 days after LAD ligation. Excluding deaths associated with acute injury from surgery, trauma or anesthesia, significantly fewer deaths occurred in the P2X$_4$R Tg than the NTG mice. The survival benefit of cardiac P2X receptor overexpression was the result of a protective effect during this short-term post-infarction period. The survival effect was not associated with a decreased infarct size in the P2X$_4$R Tg animals since both Tg and NTG hearts have similar infarct sizes. An altered post-infarction survival was seen early or late after LAD ligation. The early survival benefit afforded by cardiac P2X$_4$ receptor overexpression may be secondary to a salutary effect on heart function during the immediate post infarct period. Consistent with this concept, the Tg animals showed an improved cardiac function with a significantly higher LVDP, +dP/dt and −dP/dt at 7 days post infarction. The heart weight/body weight ratio and the cardiac myocyte cross sectional area were lower in the Tg than in the NTG animals, providing further evidence for a beneficial effect of the cardiac P2X receptor on heart failure progression in this ischemic cardiomyopathic model. It is intriguing that a decreased cardiac hypertrophy was associated with an improved cardiac contractile performance in the P2X4R Tg mice. An association between reduced compensatory hypertrophy and enhanced LV performance was also observed in mice overexpressing nitric oxide synthase and in mice receiving allopurinol or the Rho Kinase inhibitor fasudil after LAD ligation. Conversely, others have observed an association of increased hypertrophy with LV dilation and dysfunction in Tg mice overexpressing p300 histone acetyltransferase. The association between the anti-hypertrophic effect of P2X4 receptor overexpression and its effect on contractile improvement provides support for the concept that compensatory hypertrophy, such as that occurring after infarction, may be neither necessary nor beneficial.

The salutary effect of cardiac P2X$_4$ receptor overexpression was also evident at 2 months after infarction. Both the systolic thickening of the non-infarcted wall (LVPW) and the decrease in left ventricular internal dimension at systole were greater in Tg than in NTG hearts by echocardiography. The enhanced contractile measurements were obtained even thought the infarct size was larger in the Tg than the NTG hearts. The isolated in vitro working heart preparation could not detect an enhanced global left ventricular contractile function in the post-infarction Tg vs. NTG animals at 2 months after the ligation. The reason for the difference between the in vivo echocardiographic and the in vitro working heart measurements is not clear. However, several explanations are possible. First, the in vivo measurement may be more sensitive in detecting an improved contractile function than in the in vitro method. Second, an increased contractile performance derived from the overexpressed P2X$_4$ receptor may become less evident during progression of adverse remodeling. Only a more sensitive method could detect difference in the heart function. Third, the relatively large infarct size caused a significantly reduced heart function. Although the Tg hearts showed enhanced basal contractile function in the current and previous studies, the increased contractility may not augment the remaining viable contracting myocardium to manifest a significant overall function by the in vitro method. Nevertheless, the beneficial effects of P2X receptor on the cardiac contractile function and hypertrophy during the early post-infarction period are likely responsible for the improved early survival. A continued support for the cardiac contractile performance via the cardiac P2X receptor sustained the early salutary effects during ischemic heart failure remodeling.

The increase in −dP/dt or rate of relaxation of the heart muscle in transgenic animals overexpressing the P2X$_4$ receptor suggests that activation of the cardiac P2X receptor can be used to treat diastolic heart failure. Like P2X$_4$ receptor overexpression, treatment with the N-methanocarba derivatives of AMP may be employed for individuals in need of treatment for diastolic heart failure. Diastolic heart failure caused when the heart does not fully relax, so it does not fill properly with blood. By increasing the rate of relaxation of the heart muscle, the N-methanocarba derivatives of AMP will improve cardiac function in individuals with diastolic heart failure.

Overall, the cardiac myocyte P2X receptor represents a novel pathway by which a ligand-gated cell surface ion channel can increase the SR Ca$^{2+}$ store and enhance contractile performance. Increased expression of the cardiac P2X receptor can rescue the heart failure phenotype after myocardial infarction. This beneficial effect appears to be mediated by the P2X receptor-induced increase in contractile performance and decrease in cardiac hypertrophy. The study demonstrated a novel pathway arising from a cell surface ion channel to a heart failure-rescuing therapeutic benefit.

MRS2339 and the N-methanocarba derivatives of AMP are particularly useful in the treatment of cardiac diseases responsive to activation of the cardiac P2X receptor associated with defects in cardiac contractility. It was specifically shown that MRS2339 increases survival in post-infarction treated mice. Such diseases include myocardial infarction. As used herein, myocardial infarction, commonly known as a heart attack, is a disease state that occurs when the blood supply to a part of the heart is interrupted. The resulting ischemia or oxygen shortage causes damage and potential death of heart tissue. In one embodiment, treatment with the N-methanocarba derivatives of AMP is done within the within the short-term post-infarction period. As used herein, the short term post-infarction period is within 48 hours of myocardial infarction. The advantage of treating in the short term post infarction period is to block the stimulus for cardiac hypertrophy and adverse remodeling at an early stage of the heart failure progression after myocardial infarction.

Additionally, the N-methanocarba derivatives of AMP are useful for enhancing cardiac performance by increasing cardiac muscle contractility and/or increasing diastolic cardiac muscle relaxation. Included herein are thus methods of improving cardiac contractile performance in a mammal in need thereof comprising administering a therapeutically effective amount of an N-methanocarba derivative of AMP. In one embodiment, the mammal has had or is suspected of having a myocardial infarction. In another embodiment, administering is performed within the short-term post-infarction period.

The N-methanocarba derivatives of AMP are used to treat a mammal such a human.

In one embodiment, the N-methanocarba derivative of AMP is co-administered with an additional agent such as, for example, a beta-adrenergic receptor blocker, an angiotensin receptor blocker or an angiotensin converting enzyme inhibitor.

In one embodiment, included herein is a composition comprising an N-methanocarba derivative of AMP and a pharmaceutically acceptable excipient.

For oral administration, the pharmaceutical preparation can be in liquid form, for example, solutions, syrups or suspensions, or can be presented as a drug product for reconstitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions can take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well-known in the art.

Preparations for oral administration can be suitably formulated to give controlled release of the active compound.

For buccal administration, the compositions can take the form of tablets or lozenges formulated in conventional manner.

For administration by inhalation, the compositions are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The compositions can be formulated for parenteral administration by injection, e.g., by bolus injection or continuous infusion via either intravenous, intraperitoneal or subcutaneous injection. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The compositions can be formulated into creams, lotions, ointments or tinctures, e.g., containing conventional bases, such as hydrocarbons, petrolatum, lanolin, waxes, glycerin, or alcohol. The compositions can also be formulated in rectal compositions such as suppositories or retention enemas, e.g., containing conventional suppository bases such as cocoa butter or other glycerides.

In addition to the formulations described previously, the compositions can also be formulated as a depot preparation. Such long acting formulations can be administered by implantation (e.g., subcutaneously or intramuscularly) or by intramuscular injection. Thus, for example, the compositions can be formulated with suitable polymeric or hydrophobic materials (e.g., as an emulsion in an acceptable oil) or ion exchange resins, or as sparingly soluble derivatives, for example, as a sparingly soluble salt. Liposomes and emulsions are well known examples of delivery vehicles or carriers for hydrophilic drugs.

The compositions can, if desired, be presented in a pack or dispenser device which can contain one or more unit dosage forms containing the active ingredient. The pack can for example comprise metal or plastic foil, such as a blister pack. The pack or dispenser device can be accompanied by instructions for administration.

The amount of N-methanocarba derivatives of AMP that may be combined with pharmaceutically acceptable excipients to produce a single dosage form will vary depending upon the host treated and the particular mode of administration. The specific therapeutically effective amount for a particular patient will depend on a variety of factors including the activity of the specific compound employed, the age, body weight, general health, sex, diet, time of administration, route of administration, rate of excretion, drug combination, and the severity of the particular disease undergoing therapy. In some instances, dosage levels below the lower limit of the aforesaid range may be more than adequate, while in other cases still larger doses may be employed without causing any harmful side effects provided that such higher dose levels are first divided into several small doses for administration throughout the day. The concentrations of the compounds described herein found in therapeutic compositions will vary depending upon a number of factors, including the dosage of the drug to be administered, the chemical characteristics (e.g., hydrophobicity) of the compounds employed, and the route of administration. In general terms, the N-methanocarba derivatives of AMP may be provided in an aqueous physiological buffer solution (for example, 1 cc) containing about 0.2% w/v compound for oral administration. Typical dose ranges are about 285 µg/kg of body weight per day in three divided doses; a preferred dose range is from about 42 µg/kg to about 171 µg/kg of body weight per day. The preferred dosage of drug to be administered is likely to depend on such variables as the type and extent of progression of the disease or disorder, the overall health status of the particular patient, the relative biological efficacy of the compound selected, and formulation of the compound excipient, and its route of administration, as well as other factors, including bioavailability, which is in turn influenced by several factors. For example, if the compound is metabolized in the liver or excreted in bile, some of the active compound absorbed from the gastrointestinal tract will be inactivated by the liver before it can reach the general circulation and be distributed to its sites of action. It is not believed that the N-methanocarba derivatives of AMP will be subject to this first-pass loss. Additionally, because these compounds are polar and water soluble, it is expected that they will have a small volume of distribution, and thus be readily eliminated by the kidney. Moreover, binding of the instant compounds to plasma proteins may limit their free concentrations in tissues and at their locus of action since it is only the unbound drug which equilibriums across the membrane receptor sites. It is anticipated that the phosphate moiety of the instant compounds may facilitate binding of the compounds to plasma albumins, which will in turn influence the amount of free compound available to activate muscle cell P2 purinergic receptors. However, it is expected that such binding to plasma protein will not generally limit renal tubular secretion of biotransformation since these processes lower the free drug concentration and this is rapidly followed by the association of this drug-protein complex. Another factor affecting bioavailability is the distribution of the compounds to tissues. Given the relatively small size of the compounds and their water solubility, it is anticipated that the compounds will have a relatively fast second phase of drug distribution. This distribution is determined by both the blood flow to the particular tissue of the organ, such as the heart, as well as the rate at which the compounds diffuse into the interstitial compartment from the general circulation through the highly permeable capillary endothelium (except in the brain). Due to the relative hydrophilicity of these compounds, it is anticipated that there will be no fat or other significant tissue reservoir of the compounds which would account for a third phase of distribution-accumulation.

The invention is further illustrated by the following non-limiting examples:

EXAMPLES

Materials and Methods I

Isolation of Adult Cardiac Ventricular Myocytes from WT and CSQ Mice

Mice displaying the CSQ model of severe cardiomyopathy and heart failure were bred and maintained by methods known in the art. The CSQ transgenic (TG) mice were originally provided by Dr. Larry Jones (Krannert Institute of Cardiology, Indiana University School of Medicine, Indiana), and developed hypertrophy followed by a lethal heart failure phenotype with death near the age of 3 months. Ventricular myocytes were obtained from 3-month old wild type (WT) and CSQ mice of either sex (26 WT, 47 TG) by an enzymatic dissociation procedure. Briefly, the hearts were rapidly excised from mice that had been anesthetized with pentobarbital and treated with 1000 Units of heparin. The aorta was cannulated and the heart perfused in a Langendorff apparatus with oxygenated (95% $O_2$/5% $CO_2$) $Ca^{2+}$-free solution (37° C.) for 5 minutes at a rate of 2.5 ml/min. The solution composition was: 126 mM NaCl, 4.4 mM KCl, 1.0 mM $MgCl_2$, 18 mM $NaHCO_3$, 11 mM Glucose, 4 mM HEPES, and 3 mM BDM (2,3-butanedione monoxime), (pH 7.3 adjusted with NaOH). Thereafter, the perfusing solution was changed to that containing 25 μM $CaCl_2$ and liberase (70 μg/ml, Roche Molecular Biochemicals, Inc.) for 8-10 minutes. Cells were sedimented by gravity for 10-15 minutes and the pellet was resuspended in 200 μM $Ca^{2+}$-containing Tyrode's solution (containing 3 mM BDM), allowed to settle for 30 minutes at room temperature, and suspended with Tyrode's solution containing: 135 mM NaCl, 5.4 mM KCl, 1.0 mM $CaCl_2$, 1.0 mM $MgCl_2$, 10 mM HEPES and 10 mM dextrose (pH 7.4 adjusted with NaOH). The experiments were carried out at room temperature (22-23° C.) and were completed within 4-6 hours after myocyte isolation.

Cellular Electrophysiological Methods

The whole cell patch-clamp technique was used for these experiments. Electrodes were prepared from borosilicate glass pipettes (1.2 mm i.d.) with a two step pulling procedure and filled with pipette solution. The pipette was connected via an Ag—AgCl wire to the head stage of an amplifier (List EPC-7, Medical Systems, Greenvale, N.Y.) controlled by a computer and Axon pClamp™ software. For voltage clamp experiments, the electrodes were filled with a solution containing: 135 mM cesium aspartate, 5 mM NaCl, 5 mM $Mg_2ATP$, 10 mM HEPES, and 10 mM EGTA (pH 7.3 adjusted with CsOH) with or without 2 mM GDPβS. Electrode resistances were 2-4 MΩ. As soon as electrical contact was established, the superfusion medium was changed to a modified Tyrode's solution (5.4 mM KCl was omitted and 10 mM CsCl and 5 μM ouabain were added to Tyrode's solution to block $K^+$ currents and the Na/K pump current, respectively). In quantifying the P2 agonist-induced current, the Tyrode's solution contained the indicated concentration of each agent. In studying the effect of a P2 receptor antagonist, both agonist and antagonist were co-applied at the indicated concentrations. The voltage clamp protocol used was a ramp voltage protocol from −100 mV holding potential to +50 mV. The ramp protocol was applied to cells at 20 s intervals for 1 minute. Three current traces from −100 mV to 50 mV were averaged to construct the I-V relationship.

Immunoblotting

Hearts from three-month old CSQ and WT mice were isolated, blotted dry, weighed, and homogenized in ice-cold buffer containing 0.25 M sucrose, 10 mM MOPS, pH=7.2 (16 ml per gram of weight) using a tissue homogenizer (Power-Gen Model 125, Fisher Scientific, Inc., Pittsburgh, Pa.). After solubilization in sample buffer, SDS-PAGE and immunoblotting were conducted as known in the art. Twenty five μg of homogenate protein were electrophoresed per gel lane using 8% polyacrylamide and transferred to nitrocellulose. For detection of the $P2X_4$ receptor, rabbit polyclonal antibody directed against a unique C-terminal sequence of the rat $P2X_4$ receptor (Alomone, Jerusalem, Israel), which cross-reacted with both the human and mouse $P2X_4$ receptors, was used. The membrane was incubated with peroxidase-coupled anti-rabbit Ig antibody (1:5000) and developed with an ECL-Plus™ kit (Amersham). The level of the $P2X_4R$ protein was quantified via a BioRad Geldoc 2000 using the Discovery Series Quantity One version 4.5.2 (BioRad, Hercules, Calif.). The quantity of the protein in each band was proportional to the sum of intensity of all pixels within the band boundary multiplied by the area of each pixel. Equal amounts of protein were loaded per gel lane, which was subsequently confirmed by Ponceau S staining of the blot and by probing with an affinity-purified goat polyclonal antibody against the carboxy termini of a broad range of actin isoforms such as the β- and α-actins (Actin, 1-19: sc-1616) (identical in human, rat and mouse).

Quantification of Myocyte Cross Section Area

Cardiac myocyte cross-section area was quantified by methods known in the art. Excised hearts were fixed in 4% paraformaldehyde, and labeled with a fluorescein-conjugated wheat germ agglutinin. Photomicrographs were taken at the mid-left ventricular wall as previously described. The images of cross-sectioned cells showing consistently round shapes were captured with Macrofire® PictureFrame (Optronics, Goleta, Calif.) and cross-section area measured with ImageProPlus® (MediaCybernetics, Silver Spring, Md.). Typically, 50 to 100 cross-sectional areas were determined and averaged per heart.

MRS2339 and Vascular Reactivity

Thoracic aortas were quickly removed from 8 to 10-week wild type (C57 BL6) mice, cut into 3 mm rings. After pre-constriction with phenylephrine (1 µM), increasing concentrations of acetylcholine or MRS2339 were added in a cumulative fashion to achieve a concentration-response curve. The % relaxation was determined as % decrease in ring tension (gram) compared to the tension before the addition of acetylcholine or MRS2339. Data were shown as mean±SEM.

Drugs and Solutions

2-Methylthioadenosine 5'-triphosphate (2-meSATP), Brilliant Blue G (B. Blue G or BBG; pyridoxal-phosphate-6-azophenyl-2',4'-disulphonic acid, and 2-methylthioADP (2-meSADP) were obtained from Sigma Chemical Co (St. Louis, Mo.). NF449, 4,4',4'',4'''-[carbonylbis(imino-5,1,3-benzenetriyl-bis(carbonylimino))]tetrakis-1,3-benzenedisulfonic acid, was from Tocris Bioscience (Ellisville, Mo.). Both 2-meSATP and 2-meSADP were dissolved just before each experiment. Stock solutions were prepared in phosphate-buffered saline, pH=7.4, and added to the Tyrode's solution to obtain the desired concentrations. The (N)-methanocarba derivative of 2-chloroAMP, MRS2339 ((1'S,2'R,3'S,4'R,5'S)-4-(6-amino-2-chloro-9H-purin-9-yl)-1-[phosphoryloxymethyl]bicyclo[3.1.0]hexane-2,3-diol)) and the P2Y$_1$ receptor antagonist MRS2500 ((1'R,2'S,4'S,5'S)-4-(2-iodo-6-methylamino-purin-9-yl)-1-[(phosphate)-methyl]-2-(phosphate)-bicyclo[3.1.0]hexane)) were synthesized as known in the art. These two P2 purinergic agents were characterized in detail previously. MRS2339 was dissolved in phosphate-buffered saline, pH=7.4 at 3.3 µM (200 µl total volume), filtered for sterility for in vivo administration at 6 µl per day for 28 days via a mini-osmotic pump (Alzet) implanted in the CSQ mice. The longevity of MRS2339- or vehicle-administered animals was determined and the survival difference analyzed by log rank test.

Data

Unless otherwise indicated, data were provided as mean±standard error of the mean. Student's t-test for paired or unpaired samples was used to evaluate the effects of experimental interventions; P<0.05 was taken as statistically significant.

Example 1

The Extracellular 2-meSATP-Stimulated Current was Greater in CSQ than in WT Cardiac Myocytes The activation of a P2X receptor was studied by application of 2-meSATP (3 µM) for 3-5 minutes to cells obtained from CSQ TG mice and from WT mice using the whole-cell voltage clamp protocol. The ramp voltage clamp was from −100 to +50 mV. An extracellular 2-meSATP-stimulated current was observed in WT cardiac myocytes (FIG. 1), consistent with previous findings. The same concentration of 2-meSATP (3 µM) caused a similar current that displayed a linear relation between −100 and +50 mV and reversed from inward to outward at about 0 mV in cardiac myocytes of CSQ hearts (FIG. 1), identical to that found in the WT cardiac myocyte. CSQ myocytes were more responsive than WT myocytes upon exposure to 2-meSATP in the induction of a current. Of cells that showed an induced current in response to 2-meSATP, the amplitude of the 2-meSATP-stimulated current was significantly greater in cells from CSQ than from WT hearts at −100 mV (FIG. 1, P<0.05). At −100 mV, the 2-meSATP-stimulated current was −1.28±0.15 pA/pF in CSQ myocytes (±SE, n=15 cells from 7 mice) and −0.91±0.09 pA/pF in WT myocytes (N=18 cells from 10 mice) (P<0.05). Similarly, at −90 mV and −80 mV, the 2-meSATP-evoked current was also greater in CSQ than in WT myocytes (P<0.05). That 2-meSATP-stimulated current showed similar voltage dependence and reverse potential in WT and CSQ cardiac myocytes is consistent with the presence of the same P2X current in both WT and CSQ myocytes.

Figure 2:
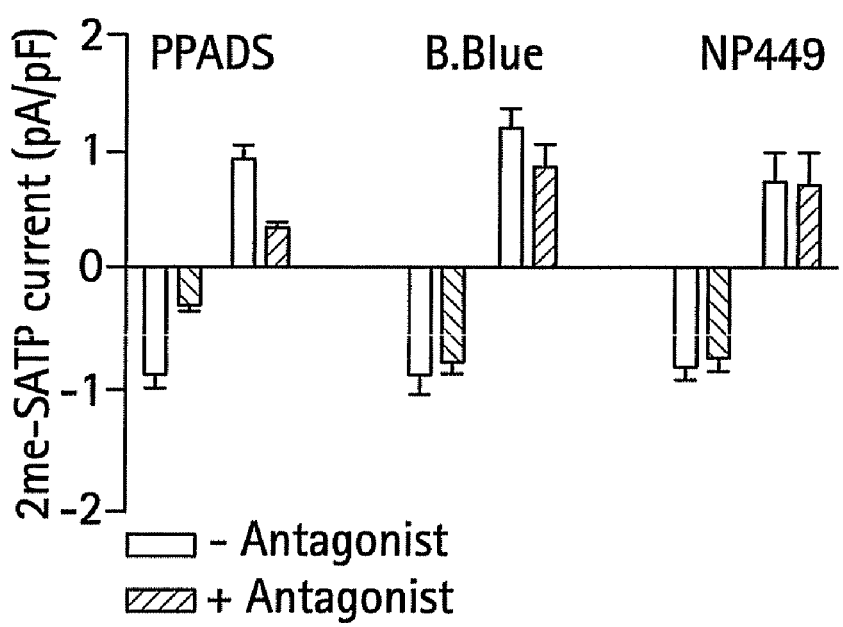
FIG. 2 shows the effects on the 2-meSATP (3 µM)-evoked current of various P2X receptor antagonists, PPADS (100 µM), NF449 (300 nM), and Brilliant Blue G (5 µM).

Additional pharmacological characterization of the 2-meSATP-evoked current was carried out. The 2-meSATP (3 µM)-evoked current of various P2X receptor antagonists PPADS (100 µM), NF449 (300 nM), and Brilliant Blue G (5 µM) were determined. The ramp voltage clamp ranged from −100 to +50 mV. Data were the mean±SEM. PPADS: 4 cells (from 6 mice); NF449: 5 cells (8 mice); B. Blue G: 5 cells (6 mice). Data summarized in FIG. 2 showed that that PPADS was able to partially inhibit the 2-meSATP-induced current while the P2X$_1$ selective antagonist NF449 or the P2X$_5$ or P2X$_7$-selective antagonist Brilliant Blue G (BBG) had very little inhibitory effect on this current. The data are consistent with the notion that homomeric P2X$_1$, P2X$_5$ or P2X$_7$ receptors are not involved in mediating the 2-meSATP-evoked current.

Example 2

Figure 3:
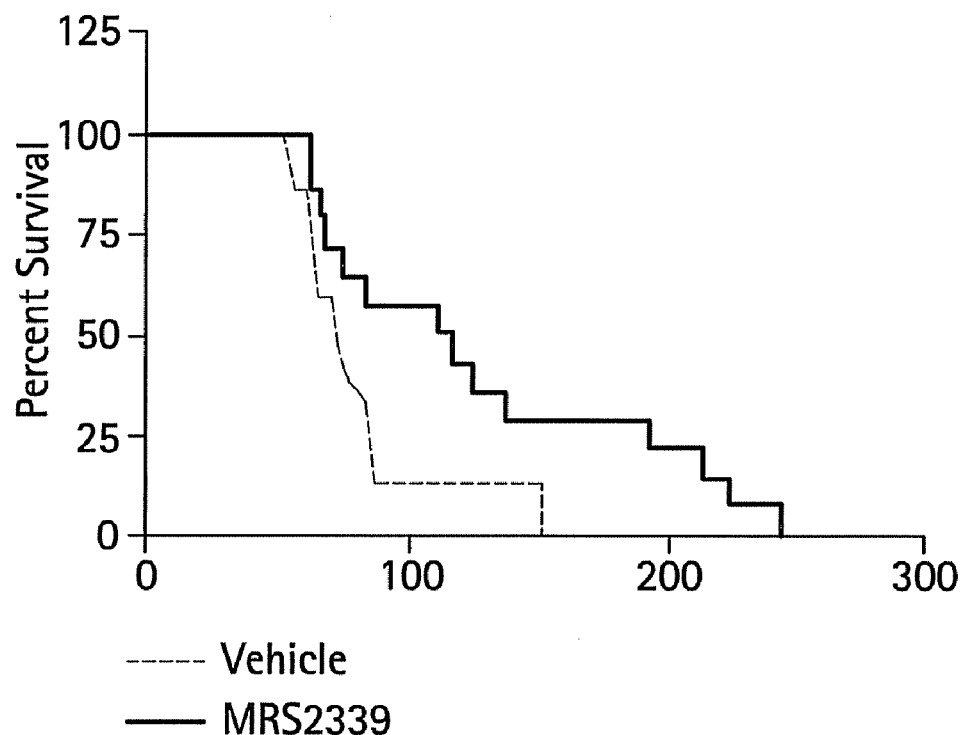
FIG. 3 shows the effects on lifespan and cardiac hypertrophy from chronic administration of MRS2339 in CSQ mice. Kaplan Meier analysis was used to determine the survival probability in CSQ animals receiving vehicle or MRS2339 via Alzet mini-pump.
Figure 4:
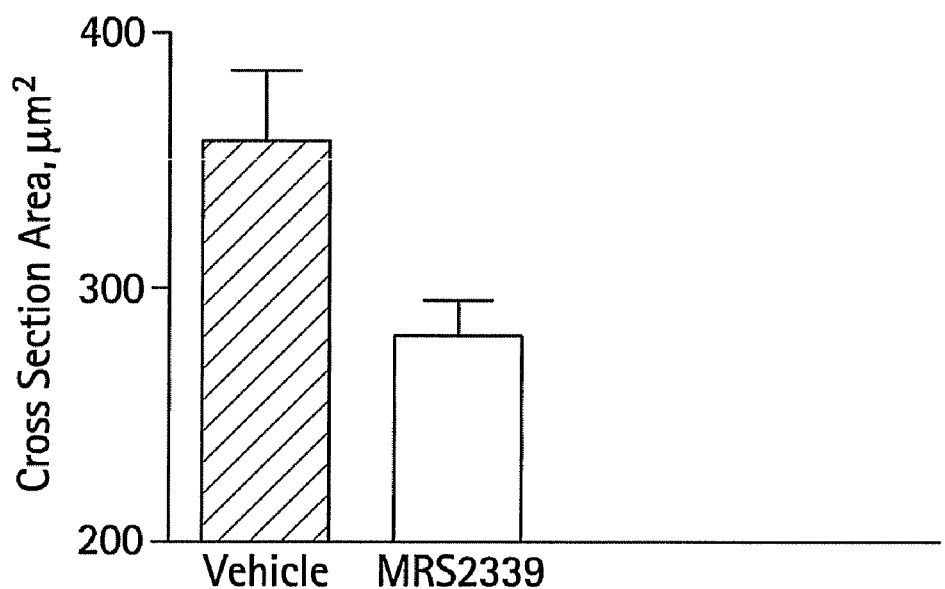
FIG. 4 shows the myocyte cross sectional areas in vehicle- and MRS2339-treated mice. Chronic treatment with MRS2339 caused a significant decrease in the cell cross sectional area ($P<0.05$).
Figure 5:
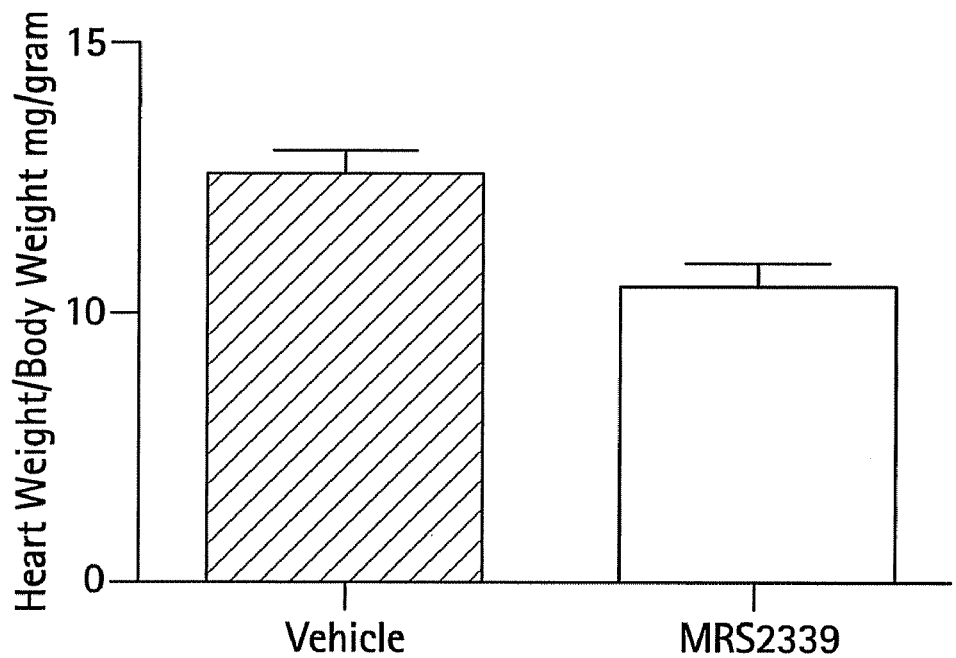
FIG. 5 shows that MRS2339 treatment decreased the heart weight/body weight ratio in CSQ mice ($P<0.05$).

Function of the Cardiac P2X Current in Heart Failure: Salutary Effect of a Nucleotidase-Resistant P2 Receptor Agonist in the CSQ Mice While the cardiac P2X current is augmented in the failing myocytes, its function in modulating the progression of heart failure is unknown. To gain insights to this question, a nucleotidase-resistant P2 receptor agonist, MRS2339, an (N)-methanocarba derivative of 2-chloroAMP, was synthesized and administered to the CSQ animals via a mini-pump. MRS2339 was infused as a 3 µM sterile solution at a rate of approximately 6 µl per day for 28 days. Log rank test method was used to analyze the survival curves (P=0.02). Compared to vehicle-injected (14 mice) CSQ mice, MRS2339-treated mice (15 mice) had a significantly longer lifespan (log rank test, p=0.02; median lifespan was 115 days in MRS2339-treated vs. 73 days in vehicle-treated animals) (FIG. 3). The improvement in survival was associated with a reduction in the cardiac myocyte hypertrophy as reflected by a smaller cross-section area in MRS2339-treated mice (281±15 µm$^2$, SE, n=6 mice) as compared to that in vehicle-treated mice (358±28 µm$^2$, n=6 mice, FIG. 4) (P<0.05). Similarly, MRS2339-treated animals exhibited a lower heart weight/body weight ratio (MRS2339-treated: 10.5±1.38, n=9 hearts vs. Controls: 12.56±2.2, n=23 hearts, P<0.05) (FIG. 5). All data were provided as mean±S.D. These data demonstrated that this nucleotide analog, when administered in vivo, can rescue the cardiac hypertrophic phenotype of the CSQ mouse.

Example 3

Figure 6:
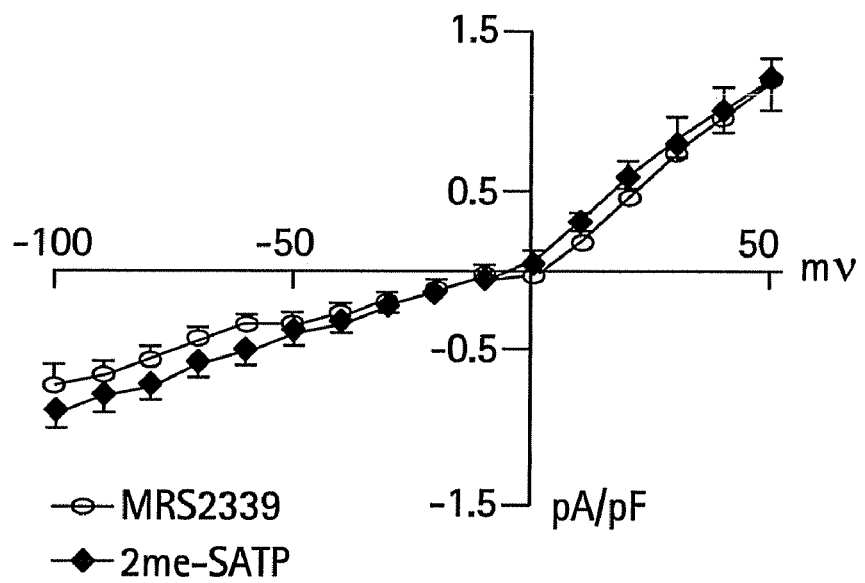
FIG. 6 shows that MRS2339 (10 µM) induced a current similar to that evoked by 2-meSATP (3 µM) in WT murine cardiac myocytes. Data were shown as current density in pA/pF. Data were mean±SEM of 18 myocytes from 10 mice for 2-meSATP-induced current and 7 myocytes from 4 mice for the current induced by MRS2339.
Figure 7:
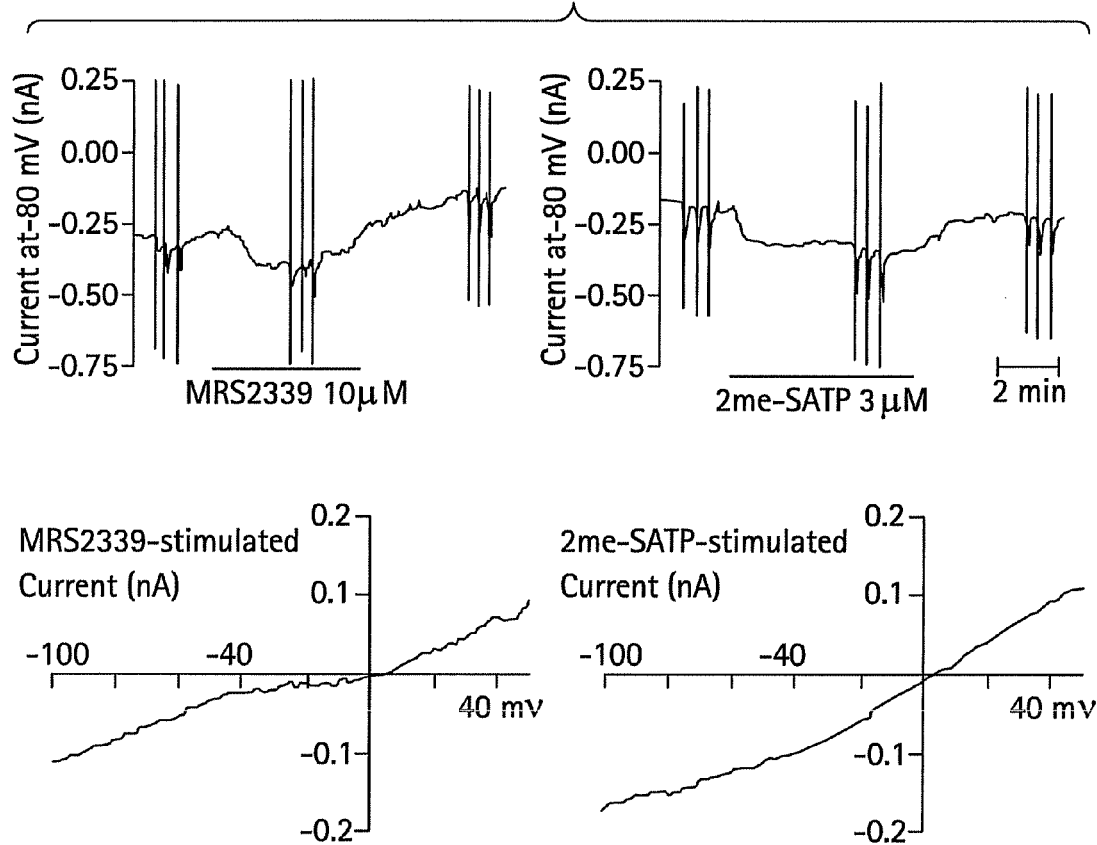
FIG. 7 shows that MRS2339 (10 µM) induced a current similar to that evoked by 2-meSATP (3 µM) with identical I-V relationships and reverse potentials in the CSQ cardiac myocyte. Addition of either MRS2339 or 2-meSATP induced an inward current on membrane currents that dissipated upon washout of agonist.

N-Methanocarba Derivative of 2-chloroAMP can Induce a P2X-Like Current in the CSQ Cardiac Myocyte Since cardiac myocyte-specific overexpression of the P2X$_4$ receptor in the CSQ mice also reduced the heart weight/ body weight ratio and cardiac myocyte hypertrophy, one possible mechanism by which MRS2339 might rescue the hypertrophic phenotype of the CSQ mice is its activation of the P2X receptor on the cardiac myocytes of these animals. In fact, this nucleotidase-resistant P2 receptor agonist can evoke a current with a similar I-V relationship and reverse potential as the P2X agonist 2-meSATP in both WT (FIG. 6) and CSQ (FIG. 7) cardiac myocytes. Cardiac ventricular myocytes were prepared from WT hearts and the current measured by voltage clamp in the whole cell configuration. (FIG. 6) Data were shown as current density in pA/pF. Data were mean±SEM of 18 myocytes from 10 mice for 2-meSATP-induced current and 7 myocytes from 4 mice for the current induced by MRS2339. Cardiac ventricular myocytes were prepared from CSQ hearts and the effects of MRS2339 and 2-meSATP on the current measured by voltage clamp in the whole cell configuration. (FIG. 7) The ramp voltage clamp was from −100 to +50 mV. Cells were held at −80 mV with ramp voltage clamp protocol. Data were shown as current density in pA/pF. Data were mean±SEM of 15 myocytes from 7 mice for the 2-meSATP-induced current and 8 myocytes from 5 mice for the current evoked by MRS2339.

Figure 8:
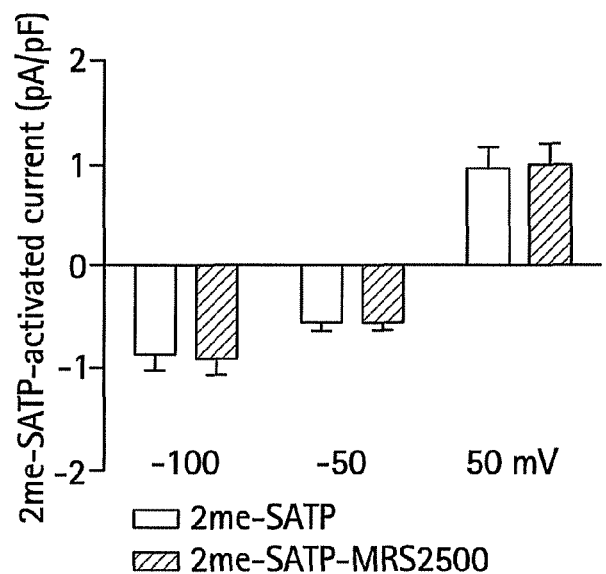
FIG. 8 shows that the potent $P2Y_1$ receptor-selective antagonist MRS2500 could not block the current evoked by 2-meSATP. The $P2Y_1$ receptor does not mediate the current evoked by 2-meSATP.
Figure 9A:
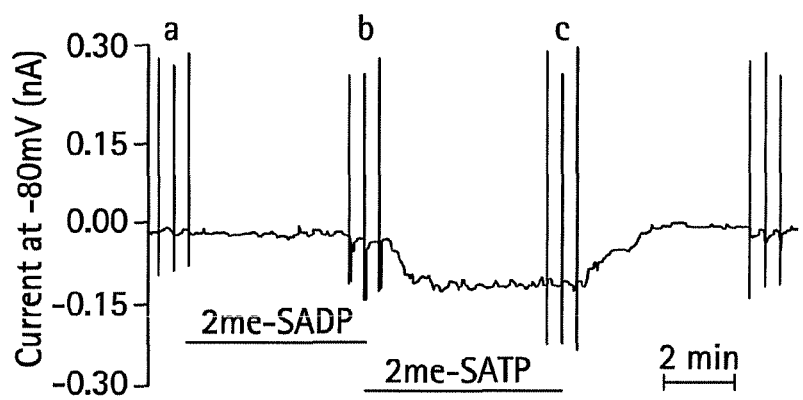
FIG. 9. A. 2-meSATP, but not 2-meSADP, was able to induce a steady inward current in an adult (3-month) mouse cardiac myocyte held at −80 mV. Both agonists were present at 3 µM. The current induced by 2-meSATP reversed upon washout of the agonist. The vertical marks on the current trace are ramp voltage clamps from −100 to +50 mV. B. The I-V relations taken at a and b (for 2-meSADP) and at a and c (for 2-meSATP) in panel A were subtracted and the differences were plotted as a function of the voltage in pA/pF. Data were shown as means±SEM from 8 WT cardiac myocytes from 14 mice.
Figure 9B:
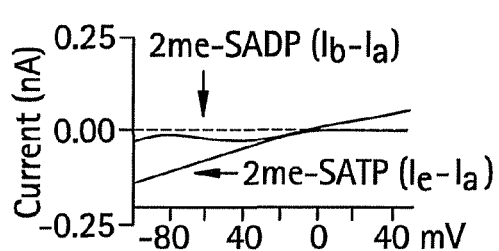
Figure 9C:
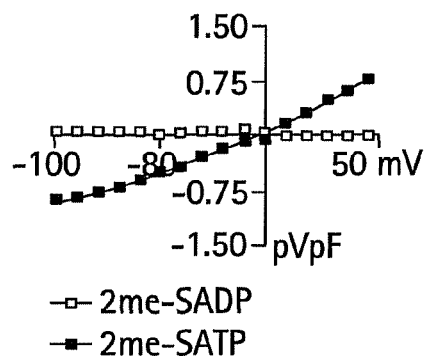

MRS2339 was initially characterized as a weak $P2Y_1$ receptor agonist. However, the potent $P2Y_1$ receptor-selective antagonist MRS2500 could not block the current evoked by 2-meSATP (FIG. 8) or by MRS2339 (data not shown). Cardiac ventricular myocytes were prepared from WT hearts and the effect of MRS2500 (1 µM) on 2-meSATP-evoked current measured by voltage clamp in the whole cell configuration. 2-meSATP was present at 3 µM. The ramp voltage clamp was from −100 to +50 mV as described in Methods I. The 2-meSATP-evoked current was similar whether or not MRS2500 was present. Data were shown as current density in pA/pF and were mean±SEM of 4 myocytes from 4 mice. This data suggests against a role of the $P2Y_1$ receptor in mediating the cardiac current effect of 2-meSATP or MRS2339. That 2-meSATP is in some systems an antagonist at the $P2Y_1$ receptor, but was a potent agonist at inducing this current further argues against a role for the $P2Y_1$ receptor in mediating this current. It is possible that 2-meSATP could be degraded to 2-meSADP which in turn might evoke a current via its activation of the $P2Y_1$, $P2Y_{12}$ or $P2Y_{13}$ receptors, if these P2Y receptors were indeed present on the murine cardiac myocyte. However, 3 µM 2-meSADP failed to induce any current in myocytes that showed a full response to 3 µM 2-meSATP (FIG. 9), further arguing against a role of the P2Y receptor in mediating the current effect of 2-meSATP. Finally, the presence of GDPβS in the pipette solution did not affect the ability of 2-meSATP to evoke the current (current without GDPβS: −0.908±0.09 pA/pF and 1.1±0.175 pA/pF at −100 and +50 mV respectively, n=18 myocytes from 22 mice; current with GDPβS: −0.877±0.198 pA/pF and 0.85±0.193 pA/pF at −100 and +50 mV respectively, n=5 myocytes from 7 mice) (P>0.05). Similarly, the addition of GDPβS in the pipette also did not decrease the MRS2339-evoked current. At −100 mV, current density was −0.73±0.15 pA/pF in the absence of GDPβS (n=7 cells); with GDPβS, the current density was −0.66±0.10 pA/pF (n=3 cells, P>0.1 vs. no GDPβS). At +50 mV, there was also no difference in the current density whether or not GDPβS was added. The data argue against a role of G protein or G protein-coupled P2Y receptors in the induction of this current.

Example 4

MRS2339 Lacks Vasodilator Effect in Mouse Aorta Preparation

Figure 10:
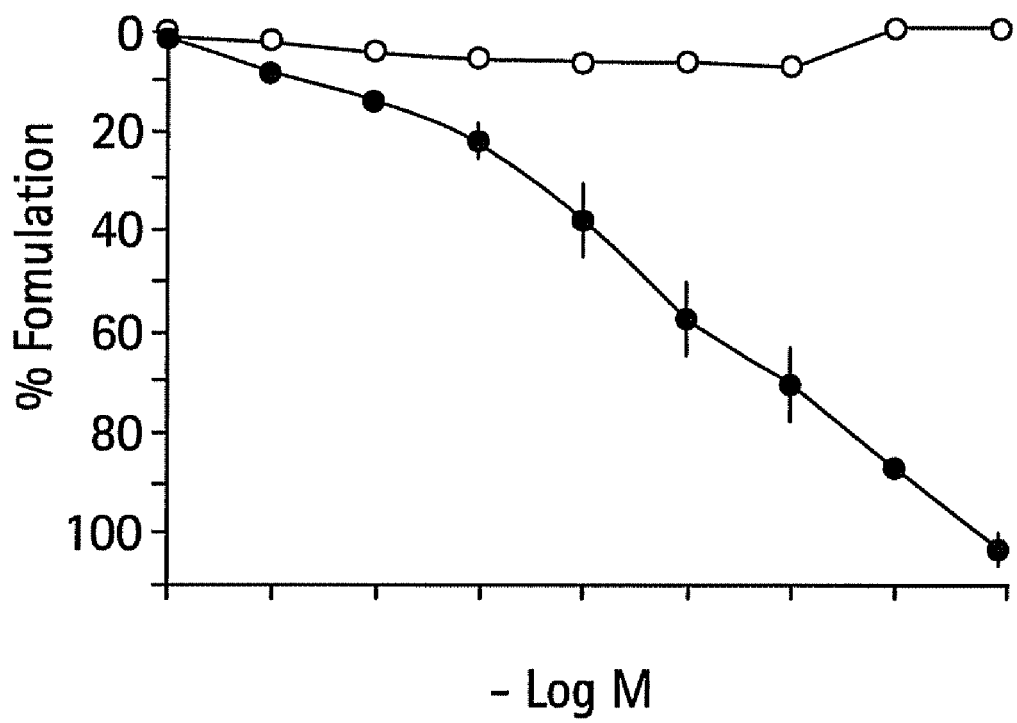
FIG. 10 shows that MRS2339 lacks vasodilator effect in adult mouse aorta ring. Adult (2-3 months old) wild type mouse thoracic aorta ring segments were studied in organ chambers. Relaxation in response to various indicated concentrations of acetylcholine and MRS2339 were determined.

Since MRS2339 is a nucleotide analog, it may in theory have a vascular effect via activation of either vascular P2Y or P2X receptors. An arterial vasodilator effect of MRS2339 would unload the failing heart and potentially explain the decrease in heart hypertrophy and the increase in lifespan of the CSQ animals. Using adult mouse thoracic aorta ring preparation pre-constricted with phenylephrine, acetylcholine was able to cause a dose-dependent relaxation of the ring segments (FIG. 10). Seven ring segments from three mice were used. Data were shown as mean±SEM. Acetylcholine caused a significant and pronounced relaxation while MRS2339 did not elicit relaxation. In the same vessel rings, MRS2339 did not induce relaxation over the same range of concentrations ($10^{-9}$ to $10^{-5}$ M). These data suggest against a vasodilator effect of MRS2339 and make it unlikely that vascular unloading is a beneficial mechanism here.

Example 5

Figure 11:
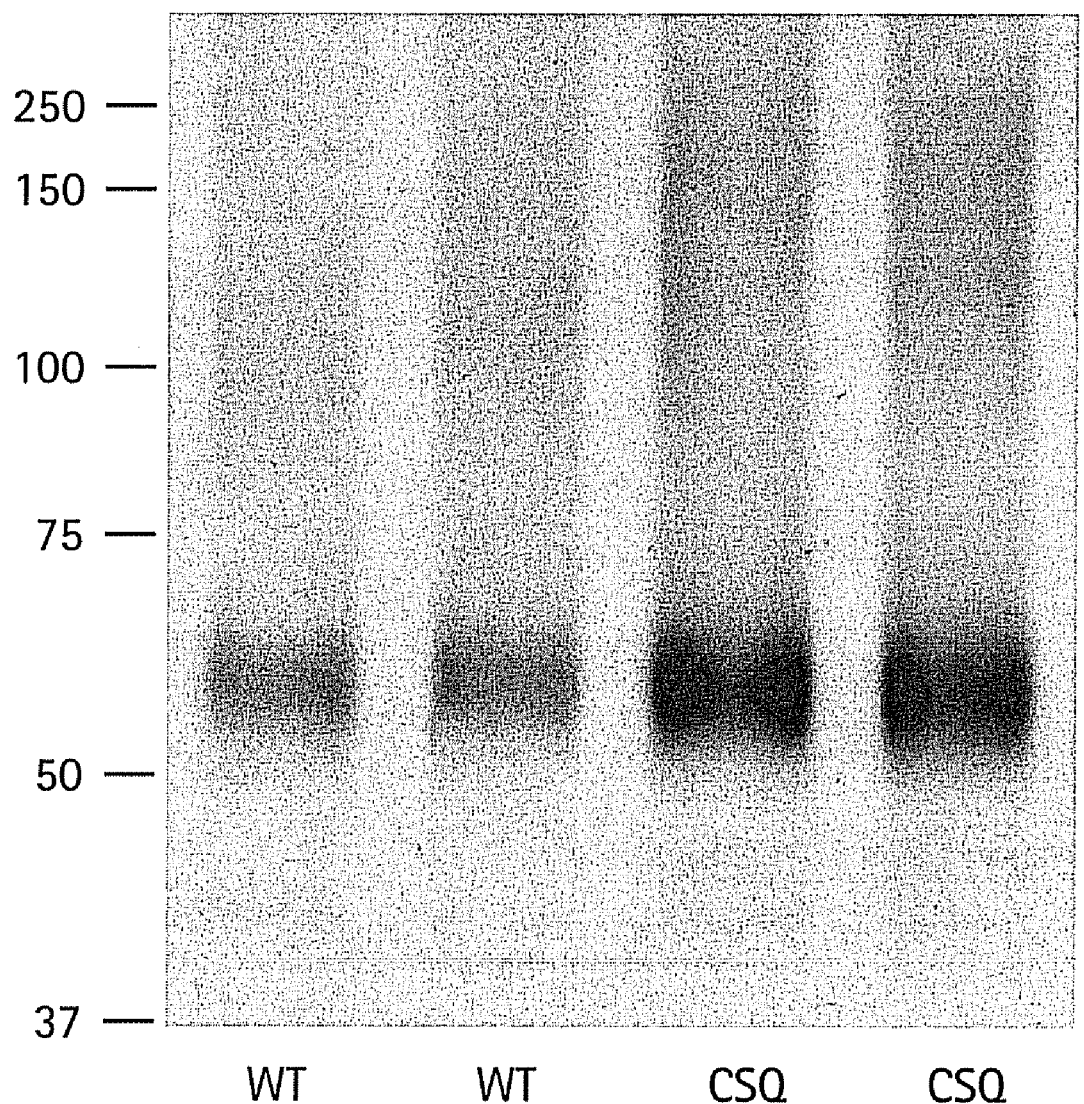
FIG. 11 shows that the $P2X_4$ receptor level is increased in the failing CSQ hearts. Hearts of three-month WT and CSQ mice were homogenized, solubilzed, immunoblotted, and relative level of $P2X_4$ receptor quantified.

Increased Expression of Endogenous Cardiac $P2X_4$ Receptors in the CSQ Mice $P2X_4$ receptors are an important subunit of the native cardiac P2X receptors. The protein expression level of this receptor in the WT and CSQ hearts was determined by immunoblotting. Identical amounts of protein were loaded per lane for each antibody used. Antibodies were specific for $P2X_4$ receptor. The autoradiograph was typical of four similar experiments. The level of $P2X_4$ receptor was higher in the CSQ than in the WT hearts (P<0.05, t-test). FIG. 11 showed that the level of cardiac $P2X_4$ receptors is greater in the CSQ than in the WT animals (P<0.05). The data are consistent with a greater level of the native P2X receptor in the CSQ heart and may provide an explanation for the greater 2-meSATP-stimulated current in these failing cardiac myocytes.

Materials and Methods II

Isolation of Adult Mouse Cardiac Ventricular Myocytes from $P2X_4$ Receptor Tg Mice Ventricular myocytes were obtained from 3-month old $P2X_4R$ Tg mice by an enzymatic dissociation procedure as known in the art. The hearts were rapidly excised from mice that had been anesthetized with pentobarbital and treated with 1000 Units of heparin. The aorta was cannulated and the heart perfused in a Langendorff apparatus with oxygenated (95% $O_2$/5% $CO_2$) $Ca^{2+}$-free solution (37° C.) for 5 minutes at a rate of 2.5 ml/min. The solution composition was: 126 mM NaCl, 4.4 mM KCl, 1.0 mM $MgCl_2$, 18 mM $NaHCO_3$, 11 mM Glucose, 4 mM HEPES, and 3 mM BDM (2,3-butanedione monoxime), (pH 7.3 adjusted with NaOH). Thereafter, the perfusing solution was changed to that containing 25 µM $CaCl_2$ and liberase (70 µg/ml, Roche Molecular Biochemicals, Inc.) for 8-10 minutes. Cells were then exposed to a stepwise increase in extracellular calcium from 0.025, 0.2 and then 1.0 mM, allowed to settle for 30 minutes at room temperature, and finally suspended with Tyrode's solution containing: 135 mM NaCl, 5.4 mM KCl, 1.0 mM $CaCl_2$, 1.0 mM $MgCl_2$, 10 mM HEPES and 10 mM dextrose (pH 7.4 adjusted with NaOH). The experiments were carried out at room temperature (22-23° C.) and were completed within 4-6 hours after myocyte isolation.

Estimation of Sarcoplasmic Reticulum (SR) $Ca^{2+}$ Content

The $Ca^{2+}$ content of the SR was obtained from experiments with caffeine. This alkaloid not only releases $Ca^{2+}$ from the SR, but also prevents its reuptake. Three 300 ms conditioning stimuli (−80 to +50 mV) at 0.2 Hz were applied to cells. At 2 seconds after the last stimulus, 10 mM caffeine was applied rapidly from a superfusion pipette within 50 µm of the test cell. With the membrane held at −80 mV, the $Ca^{2+}$ released by caffeine induces a large inward current via the Na/Ca exchanger. Integration of this inward current provides an estimate of SR $Ca^{2+}$ content. Baseline of the current was defined as that measured at ~2500 ms from the peak current and was used for current transient integration. After a control test with caffeine, 2-meSATP (3 µM) was applied for 3 minutes and caffeine was rapidly superfused again. Data were taken only from those cells that could be held during the control period, in the presence of 2-meSATP and after washout. The caffeine-induced inward current via the Na/Ca exchanger has been used previously to estimate the SR Ca content in adult mouse ventricular myocytes.

LAD Ligation and Induction of Myocardial Infarction

Ligation of LAD in anesthetized mice was carried out using procedures similar to those previously described in the art. Adult WT (BL6) or $P2X_4R$ Tg mice 12-14 weeks old of either gender were anesthetized with ketamine (100 mg/kg) and xylazine (5 mg/kg) intraperitoneally. Under a dissecting microscope, mice were placed in a supine position on a heated pad to keep body temperature at 37° C. After endotracheal intubation, the cannula was connected to a small rodent ventilator (Hugo Sachs-Harvard Apparatus, Minivent Type 845, Holliston, Mass.) on room air with a stroke volume of 0.3 ml at a rate of 160 per min. A left intercostals thoracotomy was performed and myocardial infarction was produced by ligating the left anterior descending coronary artery with an 8-0 nylon suture within 2 mm below the edge of left atrium near the origin of the artery. The ligation was deemed successful when the left anterior wall turned pale and the ligation was aimed to induce a 30-40% infarct size. Animals were used according to the approved protocols of the Institutional Review Board at University of Connecticut School of Medicine.

Measurements of Intact Heart Function, Myocyte Cross Sectional Area, Cyclic AMP Level, and Infarct Size Various parameters of intact heart function, such as left ventricular developed pressure (LVDP), rates of contraction and relaxation (±dP/dt), were quantitatively determined using the working heart model as described in the art. In brief, the aorta was cannulated with a 20-gauge catheter, positioned about 2 mm above the coronary ostia and a column of KHS buffer produced a constant hydrostatic pressure of 55 mmHg. The opening of the pulmonary vein was connected via a PE-50 catheter to a reservoir of KHS buffer that maintained a "venous return" flow into the left atrium of about 5 ml/min under the resting condition. The left ventricular developed pressure (LVDP) was the difference between LV systolic and diastolic pressures. The basal heart rate was determined in the absence of pacing.

Cardiac myocyte cross-section area was quantified according to a previously described method. Photomicrographs were taken at the mid-left ventricular wall as previously described. The images of cross-sectioned cells were captured with Macrofire® PictureFrame (Optronics, Goleta, Calif.) and cross-section area measured with ImageProPlus® (MediaCybernetics, Silver Spring, Md.). Typically, 100 cross-sectional areas were determined and averaged per heart.

Cyclic AMP was determined with an enzymatic immunoassay kit (EIA, Direct Biotrak EIA kit) according to manufacturer's instructions. The method has been used to estimate cAMP level in dispersed mammalian cardiac ventricular myocytes. In brief, 3-month $P2X_4R$ Tg myocytes were isolated and plated in laminin-coated 96 well plate at a density of 1000 cells/well, equilibrated for 1 hour at 37° C., incubated with either phosphate-buffered saline (pH=7.4) or 10 µM 2-meSATP for 10 minutes, and processed for acetylation and subsequent cAMP EIA. cAMP levels were normalized to proteins in each individual well.

The infarct size was quantified as known in the art. After fixing in 10% formalin, left ventricle was cut into five transverse sections from apex toward the base. Sections were embedded in paraffin, cut into 4 µm slices and stained with Masson trichrome to measure area of fibrosis (infarcted myocardium). The lengths of the infarcted and noninfarcted endocardial and epicardial surfaces were traced with a planimeter image analyzer (ImageProPlus®). Infarct size was calculated as the ratio of infarct length to the circumference of both the endocardium and the epicardium.

Echocardiography

Transthoracic echocardiography was performed using a linear 30-MHz transducer according to manufacturer's instructions (Vevo 660 High Resolution Imaging System from VisualSonics, Toronto, Canada). Mice were anesthetized with 1% isoflurane using a vaporizer. LV end-diastolic (LVEDD) and end-systolic (LVESD) diameters, end-diastolic and systolic septal and posterior wall thickness were measured.

Determination of Contraction Shortening and Calcium Transients in Isolated Cardiac Myocytes.

Myocyte contraction shortening (CS) by changes in sarcomere length and $Ca^{2+}$ transients were recorded from single isolated myocytes using epi-fluorescence inverted microscope with Ionoptix software and camera (Ionoptix, Milton, Mass., USA). Myocytes were placed onto a perfusion chamber attached to the stage of the inverted microscope (Zeiss IM). Cells were superfused with Tyrode's solution at 25° C. Myocytes were field stimulated with steady-state trains of stimuli at the frequencies indicated. Sarcomere length within the user-determined window was determined. Contraction shortening was determined as the difference between peak systolic length and maximum diastolic length. $Ca^{2+}$ transients were measured using the ratiometric dye, fura-2 AM. Myocytes were loaded with 2 mM of fura-2 AM for 20 minutes at 25° C. Cells were separated from fura-2 AM containing solution by sedimentation and re-suspension in fura-2-free Tyrode's solution containing 0.1 mM $Ca^{2+}$ for 20 minutes for de-esterification. $Ca^{2+}$ transients were recorded as the fluorescence ratio at 510 nm in response to excitation from 340 and 380 nm. $Ca^{2+}$ transients were digitized and analyzed. $Ca^{2+}$ transients and CS were measured simultaneously in the same myocytes.

Drugs and Solutions

2-Methylthioadenosine 5'-triphosphate (2-meSATP) and ATP were obtained from Sigma Chemical Co (St. Louis, Mo.). Fura-2 AM was obtained from Molecular Probes (Eugene, Oreg.) and used according to manufacturer's instructions to measure intracellular calcium concentration. Stock solutions were prepared in phosphate-buffered saline, pH=7.4, and added to the Tyrode's solution to obtain the desired concentrations. CyclicAMP EIA kit was from GE Healthcare (Piscataway, N.J.). The $P2X_4R$ transgenic construct was generated by subcloning a 1.8-kb Hind III fragment of human $P2X_4$ receptor cDNA ($hP2X_4R$) into Hind III site of α-MyHC expression vector and bred in B6SJL mice.

Data

Unless otherwise indicated, data were provided as mean±standard error of the mean. Student's t-test for paired or unpaired samples was used to evaluate the effects of experimental interventions; $P<0.05$ was taken as statistically significant.

Example 6

Figure 12:
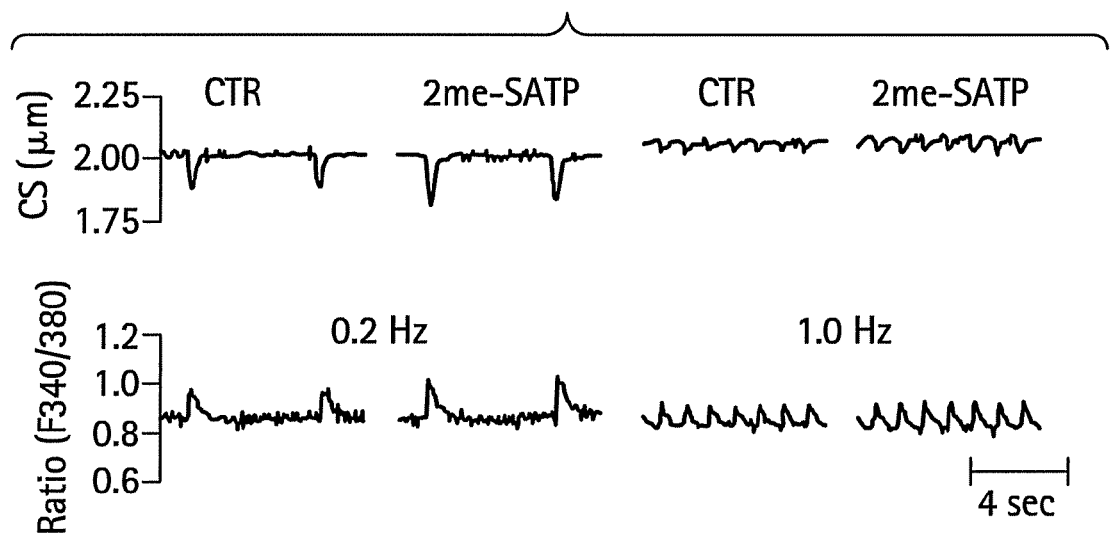
FIG. 12 shows the contraction shortening (CS) transients and $Ca^{2+}$ transients in response to 2-meSATP (3 µM) in P2X$_4$R Tg cardiac myocytes. The CS and Ca$^{2+}$ transients increased significantly as compared to the basal control levels.
Figure 13:
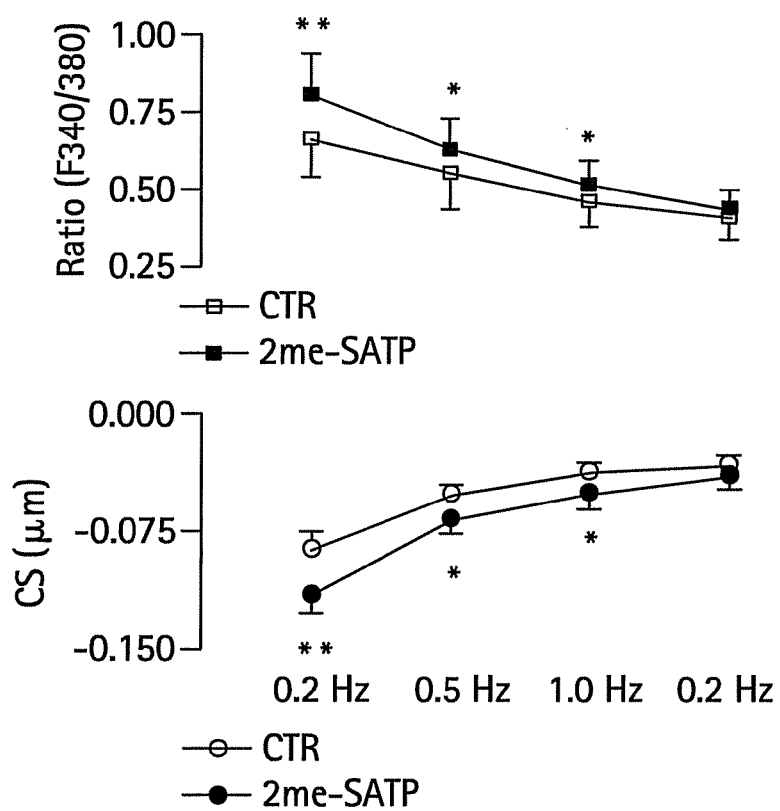
FIG. 13 shows the CS and Ca$^{2+}$ transients in response to 2-meSATP (3 µM) in adult mouse myocytes. The CS and Ca$^{2+}$ transients increased significantly as compared to the basal control levels.
Figure 14:
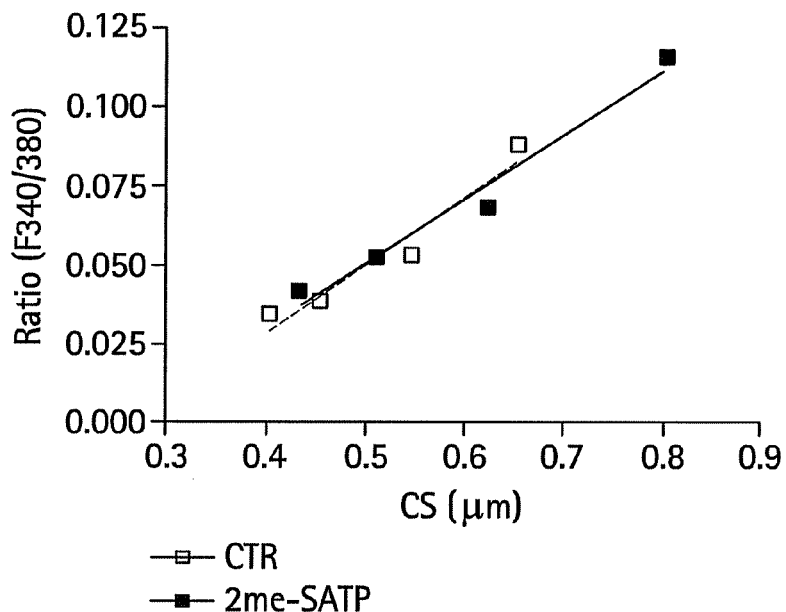
FIG. 14 is a plot of the change in Ca$^{2+}$ fluorescence vs. that in CS before exposure to the P2X agonist 2-meSATP.

Cardiac P2X Receptor-Mediated Increase in Myocyte Contractility is Associated with a Concomitant Increase in Intracellular Calcium Transients P2X$_4$R Tg cardiac myocytes demonstrated a significant increase in the extent of contraction shortening (CS) in response to extracellular 2-meSATP at 0.2, 0.5, and 1.0 Hz (FIG. 12) (at 0.2 Hz, basal=0.087±0.011 μm vs. 2-meSATP=0.116±0.011 μm, p<0.01 paired t test, n=9 myocytes from 8 mice; at 1.0 Hz, basal=0.038±0.007 μm vs. 2-meSATP=0.052±0.01 μm, p<0.05). Consistent with a negative force-frequency relationship in the adult murine cardiac myocytes, the extent of CS was reduced under basal and 2-meSATP-stimulated conditions (FIG. 13). The P2X receptor-mediated increase in CS was associated with an increase in the intracellular calcium transients, assessed as fluorescence ratios at various frequencies of pacing (FIGS. 12 and 13) (at 0.2 Hz, basal fluorescence ratio=0.66±0.12 vs. ratio in presence of 2-meSATP=0.81±0.13, P<0.01, paired t test, 9 myocytes; at 1.0 Hz, basal=0.45±0.081 vs. 2-meSATP=0.51±0.08, P<0.05). The plot of change in calcium fluorescence vs. that in CS in the absence of P2X agonist was super-imposable on the plot obtained in the presence of the agonist (FIG. 14). The slope without extracellular 2-meSATP (0.21±0.036) was similar to that with 2-meSATP (0.20±0.02, P>0.1). Data were the mean±SEM. The data suggest that the agonist-induced increase in myocyte contractility was not due to an increase in sensitivity to intracellular calcium.

Example 7

Figure 15:
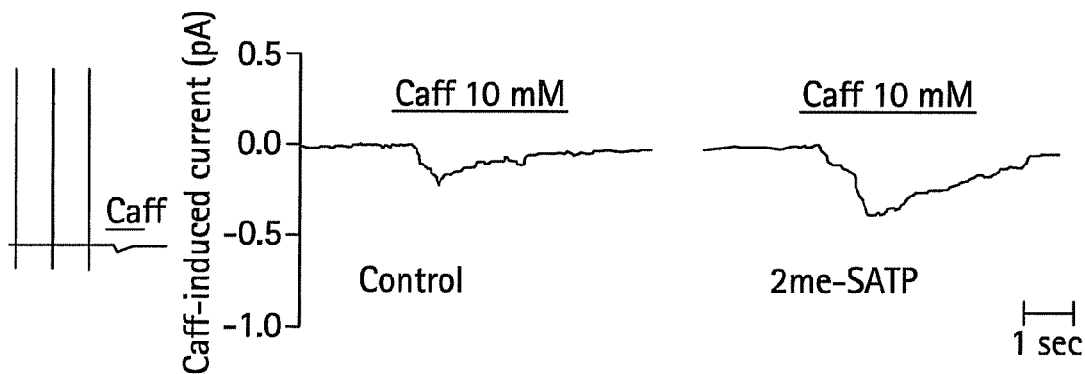
FIG. 15 shows the SR Ca$^{2+}$ content quantified by the caffeine (10 mM)-induced inward current mediated via the Na$^+$/Ca$^{2+}$ exchanger the presence of extracellular 2-meSATP (3 µM).
Figure 16:
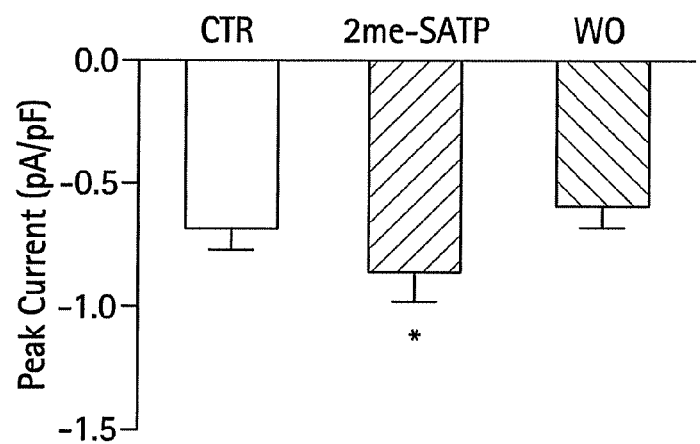
FIG. 16 shows the peak caffeine (10 mM)-induced inward current mediated via the Na$^+$/Ca$^{2+}$ exchanger the presence of extracellular 2-meSATP (3 µM).
Figure 17:
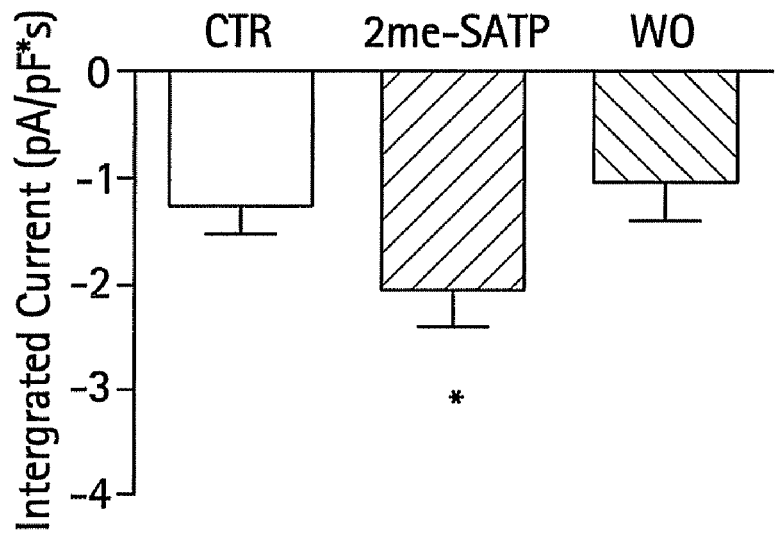
FIG. 17 shows the integrated caffeine (10 mM)-induced inward current mediated via the Na$^+$/Ca$^{2+}$ exchanger the presence of extracellular 2-meSATP (3 µM).

Stimulatory Effect of Extracellular 2-meSATP on SR Calcium Content in P2X$_4$R Tg Myocytes The P2X receptor-mediated increase in calcium transients may be the result of an enhanced SR calcium store during receptor activation. To test this hypothesis, caffeine-induced inward $I_{Na/Ca}$ was used to determine the SR calcium content in the absence and the presence of P2X agonist. FIG. 15 showed that the presence of extracellular 2-meSATP caused a significant increase in the caffeine-induced inward current (P<0.05, n=14 Tg myocytes). The increase was significant in both the peak (FIG. 16) and the integrated (FIG. 17) $I_{Na/Ca}$ inward current (P<0.05 vs. the basal control level). The P2X receptor agonist effect dissipated upon its washout. The increased caffeine-mediated inward $I_{Na/Ca}$ by 2-meSATP in P2X$_4$R Tg myocytes was not due to an increased density of the Na$^+$/Ca$^{2+}$ exchanger in the Tg myocyte since the peak and integrated $I_{Na/Ca}$ currents under basal agonist-free condition in the Tg cells (−0.66±−0.08 pA/pF and −1.24±−0.27 pA*ms/pF respectively, n=14 myocytes) were similar to those in the NTG cells (−0.66±−0.09 pA/pF and −1.25±−0.28 pA*ms/pF, P>0.1). Further, the heart weight/body weight ratio and the cardiac myocyte cross sectional areas were similar in Tg and NTG cells (data not shown). This finding argued against the possibility that variation in myocyte size may have caused an increase in caffeine-induced $I_{Na/Ca}$ in Tg vs. NTG cells. The increase in the caffeine-induced $I_{Na/Ca}$ by the P2X agonist is likely due to an enhanced loading of the SR with Ca$^{2+}$ in the Tg myocytes.

The P2X receptor-mediated increase in myocyte contractility or calcium transient occurred in the absence of any cyclic AMP (cAMP) accumulation in the P2X$_4$R Tg myocyte. 2-meSATP did not cause any increase in the intracellular cyclic AMP level in Tg cells (basal: 3.97±0.33 pmol/mg protein vs. 2-meSATP at 10 μM: 3.18±0.45 pmol/mg, P>0.1; isoproterenol: 16.6±1.53 pmol/mg, p<0.05 vs. basal or 2-meSATP, n=12 determinations from myocytes of three Tg mice). For comparison, 2-meSATP also did not stimulate any cAMP accumulation in wild type (WT) cardiac myocytes (data not shown). Previous study demonstrated that activation of the native cardiac P2X receptor in WT cells or the overexpressed P2X$_4$ receptor in Tg cells did not stimulate or inhibit the L-type calcium channel. The lack of any stimulatory effect of 2-meSATP on cAMP accumulation is compatible with its lack of stimulation of the L-type calcium channel given the known effect of cAMP on L-type calcium channel activity. Together, the data showed that activation of the cardiac P2X receptor can increase SR calcium store and intracellular calcium level with an enhanced contractile state of the myocyte in a cAMP-independent manner.

Example 8

Figure 18:
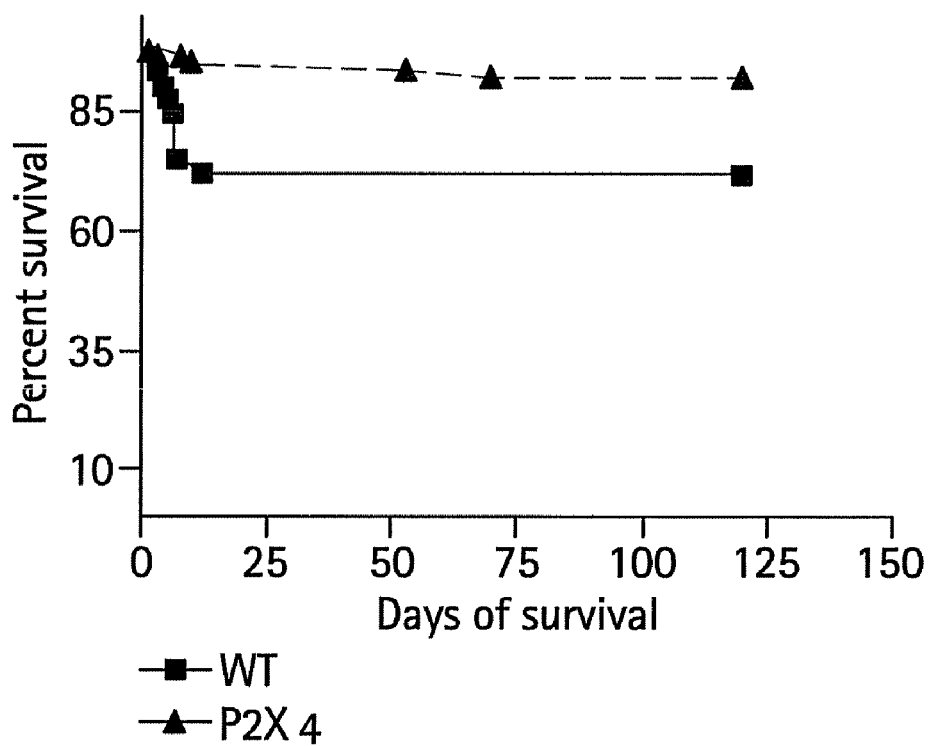
FIG. 18 shows a Kaplan Meier analysis used to determine the survival probability in P2X$_4$R Tg (65 mice) and WT (32 mice) animals after LAD ligation-induced myocardial infarction.

Cardiac-Specific Overexpression of the P2X$_4$ Receptor Enhanced Survival after LAD Ligation-Induced Myocardial Infarction P2X$_4$ receptor overexpression was able to prolong lifespan and rescue the calsequestrin model of severe cardiomyopathy. This salutary effect was associated with a P2X receptor-mediated enhancement of cardiac performance. Since the cardiac P2X receptor can induce an increase in the SR calcium content and cause an enhanced cardiac performance, the receptor may serve a generalized beneficial role in different models of heart failure. This hypothesis is compatible with the observations that the failing human cardiac myocytes exhibited decreased SR calcium store and that restoration of this content was correlated with recovery of cardiac function during ventricular assist device implantation in patients. To test a potential generalized salutary effect of P2X$_4$R activation in heart failure, the LAD ligation-mediated ischemic cardiomyopathy was induced in both WT and P2X$_4$R Tg mice. All animals that fully recovered from anesthesia and lived for 24 hours were analyzed for survival. Postoperative survival was monitored for 4 months. The overall post-infarct survival was significantly improved in P2X$_4$R Tg than WT mice (FIG. 18). The infarct sizes were similar in the two groups (WT: 38±2% infarction, n=25 vs. P2X$_4$R Tg: 34±1.7%, n=33, p=0.12). The improved survival after infarction was due to a lower incidence of death during the first 7-10 days after LAD ligation.

Example 9

Figure 19:
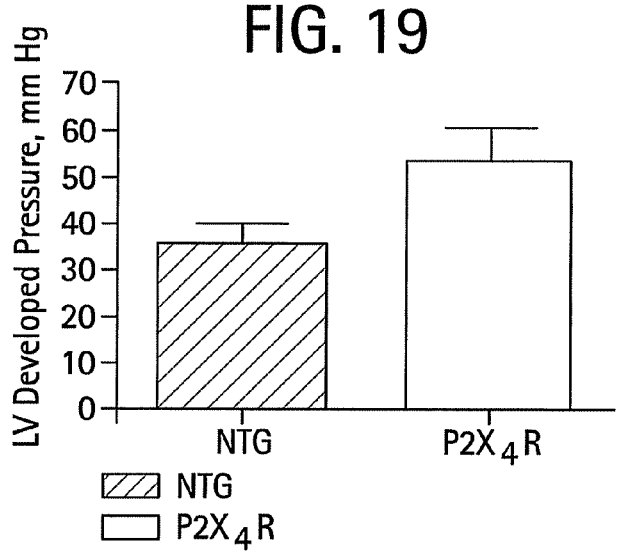
FIG. 19 shows the effects of cardiac-specific overexpression of P2X$_4$ receptors on depressed LVDP after myocardial infarction.
Figure 20:
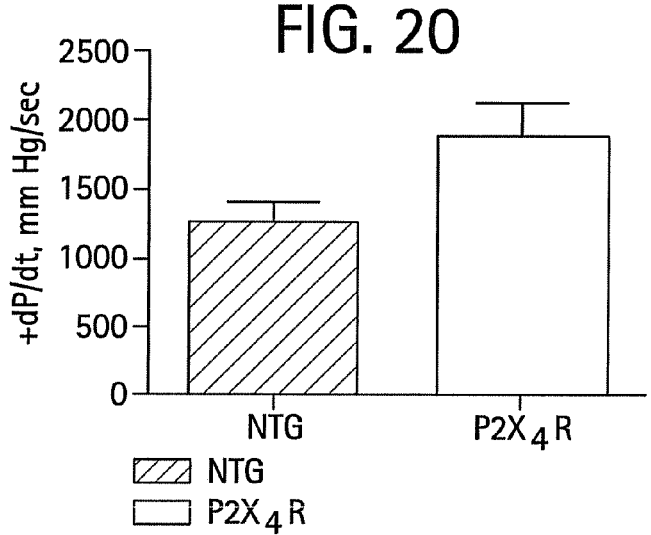
FIG. 20 shows the effects of cardiac-specific overexpression of P2X$_4$ receptors on +dP/dt after myocardial infarction.
Figure 21:
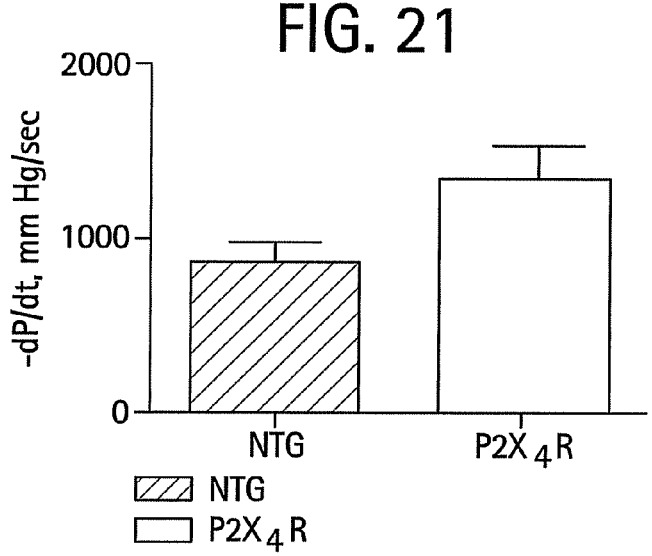
FIG. 21 shows the effects of cardiac-specific overexpression of P2X$_4$ receptors on −dP/dt after myocardial infarction.

Improved Cardiac Performance in P2X$_4$R Tg Mice Following Myocardial Infarction To further characterize the effect of P2X$_4$ receptor overexpression following infarction, cardiac function was examined in LAD-ligated P2X$_4$R Tg mice. At 7 days post infarction, the P2X$_4$R Tg mice showed enhanced left ventricular developed pressure (LVDP) (FIG. 19), +dP/dt (FIG. 20), and −dP/dt (FIG. 21) in an isolated working heart preparation.

Figure 22:
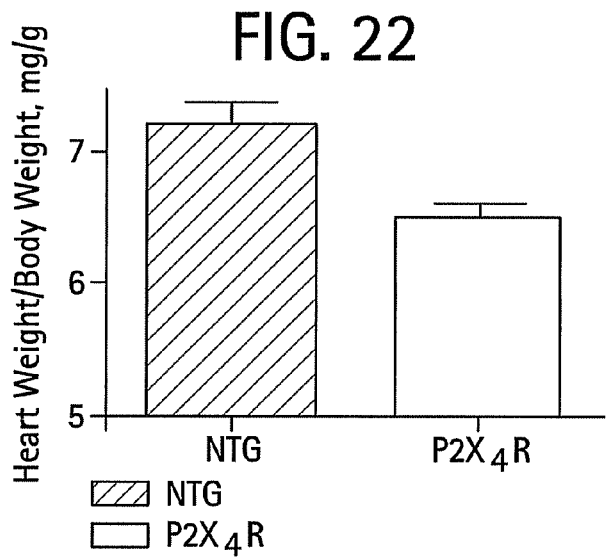
FIG. 22 shows the effects of cardiac-specific overexpression of P2X$_4$ receptors on heart weight/body weight ratio after myocardial infarction.

The salutary effect of P2X$_4$ receptor overexpression was associated with a decreased heart weight/body weight ratio (FIG. 22) as well as a reduced cardiac myocyte cross section area measured at 7 days post myocardial infarction (WT myocyte area=191±21 μm$^2$, SD, n=18 mice vs. P2X$_4$R Tg myocyte area=142.5±27 μm$^2$, n=17 mice, P<0.0001). Thus, an improved contractile function was associated with a decreased level of cardiac hypertrophy at the short-term 7 days post myocardial infarction.

Whether the cardiac contractile performance was sustained at 2 months after infarction was investigated. Echocardiographic measurements were carried out to determine the cardiac function in vivo. The baseline echocardiographic parameters, such as LVIDd and LVIDS (left ventricular internal dimension at diastole and systole respectively), LVPW (left ventricular posterior wall thickness), and IVS (septum thickness), were similar between P2X$_4$R Tg and NTG animals (P>0.1). Baseline heart weight/body weight ratios, cardiac myocyte cross sectional areas, and cell lengths were also similar in Tg vs. NTG mice (P>0.1). These data suggest a normal baseline cardiac phenotype of the P2X$_4$R Tg animals, consistent with previous findings. However, echocardiographic measured FS was significantly greater in Tg (34.3%±1.5%, n=8 mice) than in NTG (29.3%±1.2%, n=8, p=0.02) hearts, indicating an enhanced basal systolic contractile function of the Tg mice.

Figure 23:
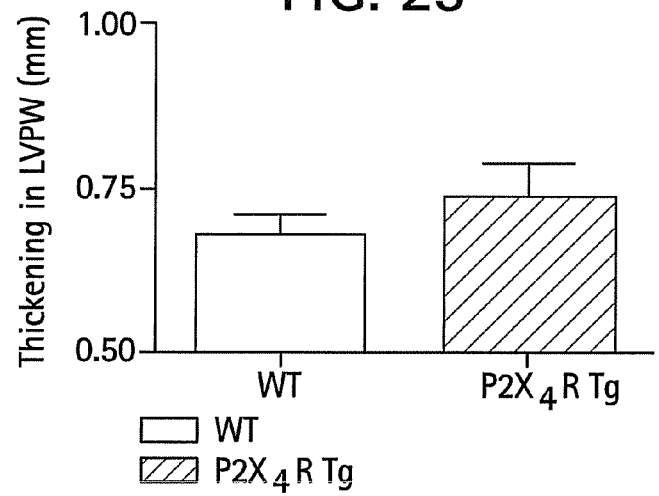
FIG. 23 shows LVPW thickness in mm in P2X$_4$R Tg vs. NTG mice at 2 months post infarction.
Figure 24:
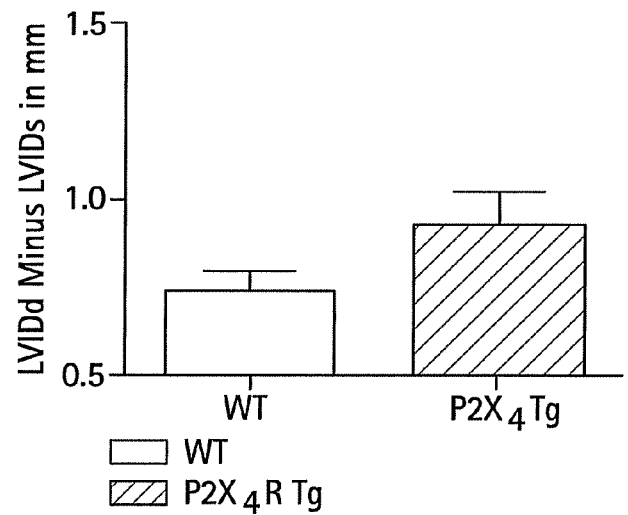
FIG. 24 shows the LVID was measured at diastole and systole and the differences between LVIDd and LVIDs in P2X$_4$R Tg vs. NTG mice at 2 months post infarction.
Figure 25:
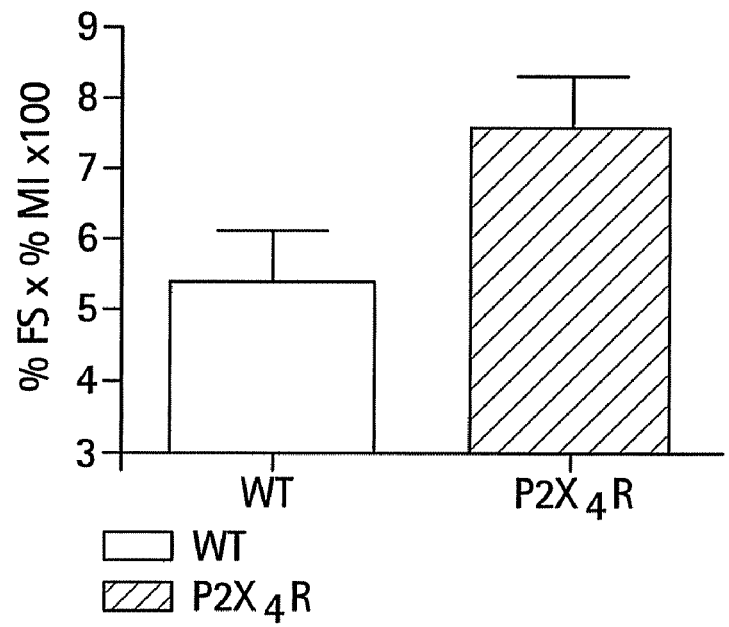
FIG. 25 shows the systolic shortening measured as fractional shortening (FS) normalized to the infarct size as the product of FS and % infarct in P2X$_4$R Tg vs. NTG mice at 2 months post infarction.

At two months after infarction, the Tg hearts showed greater systolic thickening of LVPW, representing a non-infarcted region, than did the NTG animals (P<0.05) (FIG. 23). Among the mice that had echocardiographic measurements, the infarct size was larger in Tg (39.9±2.66, n=10) than in NTG (30.2±2.4%, n=9, P<0.05) mice. Thus, despite the larger infarct in the LAD-ligated P2X$_4$R Tg animals, the Tg hearts showed improved systolic thickening of the non-infarcted LVPW. The absolute difference between the LVIDd and the LVIDs in mm was significantly greater in Tg than NTG animals (FIG. 24), reflecting a greater degree of decrease in LVID during systole in the P2X$_4$R Tg hearts. When the fractional shortening (FS) was normalized to the infarct size by obtaining the product of FS and % of infarct, the Tg hearts showed a greater normalized shortening (FIG. 25). Finally, Tg hearts showed a similar LVIDd (4.59±0.13 mm, n=10) as the NTG mice (4.46±0.12 mm, n=9, P>0.1) even though the Tg hearts had sustained a larger infarct. Although the P2X$_4$R Tg hearts did not show an increased LVDP or +dP/dt at 2 months after infarction in an isolated in vitro working heart model (data not shown), an improved in vivo cardiac contractile performance in the post-infarction Tg hearts is consistent with their enhanced basal contractile function that was sustained after the infarction.

Example 10

MRS2339 Enhanced Survival After LAD Ligation-Induced Myocardial Infarction

Figure 26:
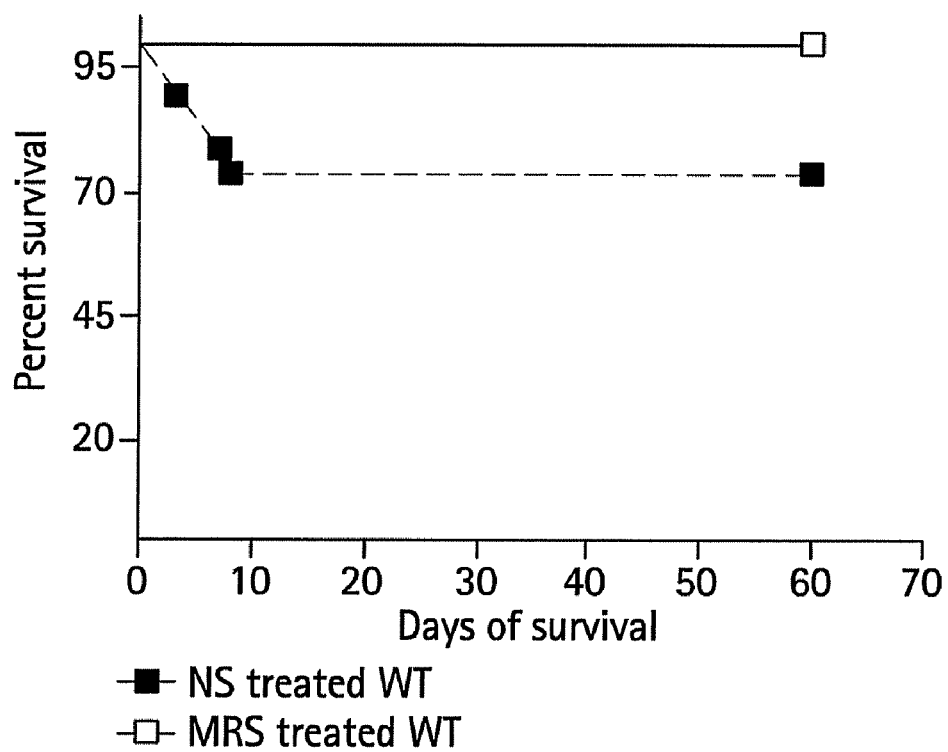
FIG. 26 shows the MRS2339 enhanced survival after LAD ligation-induced myocardial infarction.

The LAD ligation-mediated ischemic cardiomyopathy was induced in WT mice. (FIG. 26) At two days post-infarction, 15 mice were treated with MRS3229 and 19 mice were treated with NS (normal saline as the vehicle control). MRS2339 was infused as a 3 µM sterile solution at a rate of approximately 6 µl per day for 28 days. In contrast to NS, MRS3229 increased post-infarction survival to greater than 95% at up to 60 days post-infarction. The protocol was similar to those described above except that WT mice were induced to have infarct by the same LAD ligation and then were treated with MRS2339 using the same dose and route of administration as in example 2. P<0.05 by log rank test.

Example 11

Measurement of Cardiac Functions in Intact Heart Preparations

Following injection of heparin via tail vein (500 U/kg, iv) and anesthetization with nembutal (125 mg/kg for rats and 150 mg/kg for mice, ip) intraperitoneally, heart with all major vessels and lungs attached were excised. The aorta was then cannulated with a 20-gauge catheter, positioned about 2 mm above the coronary ostia. For the Langendorff method, a water-filled latex balloon (size #3) was inserted into the lumen of the left ventricle via the left atrium. The distal end of the balloon attached catheter was connected to a pressure transducer for measurement of intraventricular pressure and ±dP/dt. The balloon was inflated to a constantly held diastolic pressure of 5-7 mmHg. The retrograde perfusion via the aorta was carried out by a perfusion pump maintaining a column of Krebs-Henseleit solution (KHS; composed of, in mM, 120 NaCl, 4.7 KCl, 2.5 CaCl$_2$, 1.2 MgSO$_4$, 1.2 KH$_2$PO$_4$, 0.5 EDTA, 25 NaHCO$_3$, 2 pyruvate and 11 glucose, pH=7.4 following gassing with 95% O$_2$-5% CO$_2$ at 37° C.) to provide a constant coronary perfusion pressure of 65 mmHg. The coronary perfusion pressure was confirmed by a pressure transducer connected via a side port to the aorta perfusion cannula. Drugs were added in the KHS buffer and infused via retrograde perfusion of the coronary artery.

For the working heart model, a column of KHS buffer produced a constant hydrostatic pressure of 65 mmHg (for rat) or 55 mmHg (for mice). The opening of the pulmonary vein was connected via a PE-90 (for rat) or a PE-50 (for mice) catheter to a reservoir of KHS buffer that maintained a "venous return" flow into the left atrium of about 12 ml/min (rat) or 5 ml/min (mice) under the resting condition. The venous return was maintained by a constant level of hydrostatic pressure (7-8 mm Hg) yielding a steady rate of venous return. The entering KHS buffer was then switched from retrograde to antegrade perfusion and produced a work-performing heart preparation. The perfusate exited the left ventricle through the aorta cannula, which was connected to the aortic column of KHS buffer with a hydrostatic pressure of 55 mmHg (for mice) or 65 mm Hg (for rat). Aortic flow was the amount of perfusate exiting the aortic cannula measured in millimeters per minute. Coronary flow, in millimeters per minute, was collected via opening of the pulmonary artery. The sum of aortic flow and coronary flow was the cardiac output. A 23 gauge catheter was inserted into the left ventricle and its distal end is connected to a pressure transducer to record left ventricular pressures and +dP/dt. The left ventricular developed pressure (LVDP) was the difference between LV systolic and diastolic pressure. A side port of the reservoir allowed direct infusion of beta-adrenergic agonist isoproterenol or P2X receptor agonist 2-meSATP into the KHS buffer that entered the left ventricle via the left atrium, which then entered the coronary circulation following ejection of drug-containing perfusate into the aorta.

The pressure recordings were channeled from amplifiers which had been pre-calibrated by a transducer simulator/calibrator (Ken Scientific Corp., Litchfield, Conn.). The signals were then digitized via a PCM-DAS 16S/330 interface board (Computer Boards, Inc., Mansfield, Mass.) which provided a high level of performance with analog input channels and digital channels. Data were analyzed by computer software (WorkBench for Windows+, Kent Scientific Corp) designed for an IBM-compatible computer (Dell). The amplified and digitized signals from the transducers were constantly displayed and analyzed. Data acquisition, signal display (LV pressures, +dP/dt, heart rate), and data analysis programs were run concurrently from the hard drive of the computer. Data points under each basal condition and during infusion of each drug concentration were summarized as means±SE. Data obtained with and without drug were analyzed by paired t test for possible statistically significant differences. In comparing the effects between groups treated with two different agonists or under different conditions, unpaired t test was used.

Figure 27:
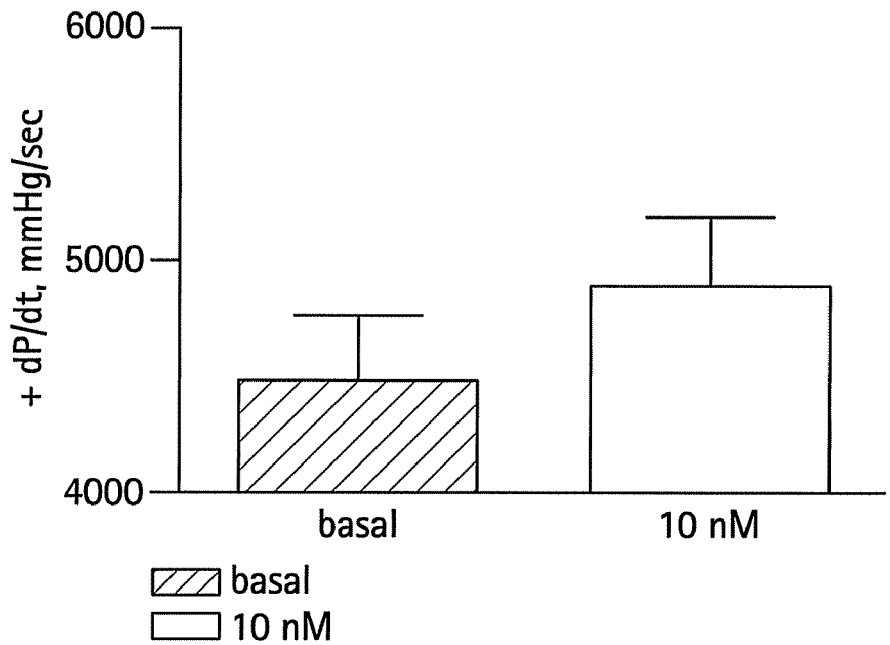
FIG. 27 shows that MRS2339 can increase +dP/dt in intact CSQ mouse hearts.
Figure 28:
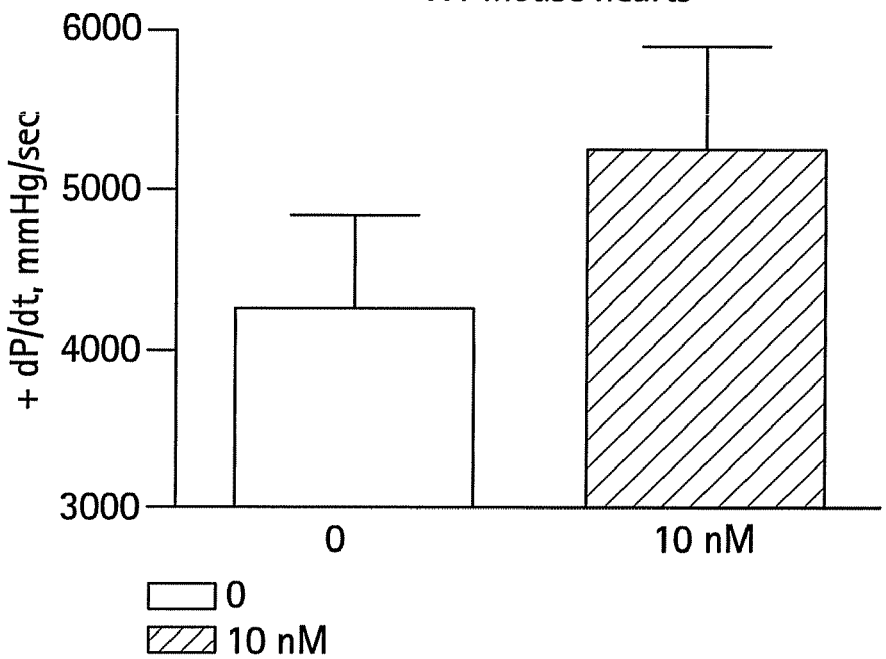
FIG. 28 shows that MRS2339 can increase +dP/dt in intact WT mouse hearts.

Data was obtained for both CSQ (FIG. 27) and WT mouse hearts (FIG. 28). MRS2339 increased +dP/dt in both CSQ and Wt hearts. It is expected that N-methanocarba derivatives of AMP such as MRS2339 will also increase –dP/dt since many compounds that increase +dP/dt will also increase the –dP/dt.

Example 12

Metoprolol Increases Lifespan in Binary $P2X_4$ Receptor/CSQ Transgenic Mice

Figure 29:
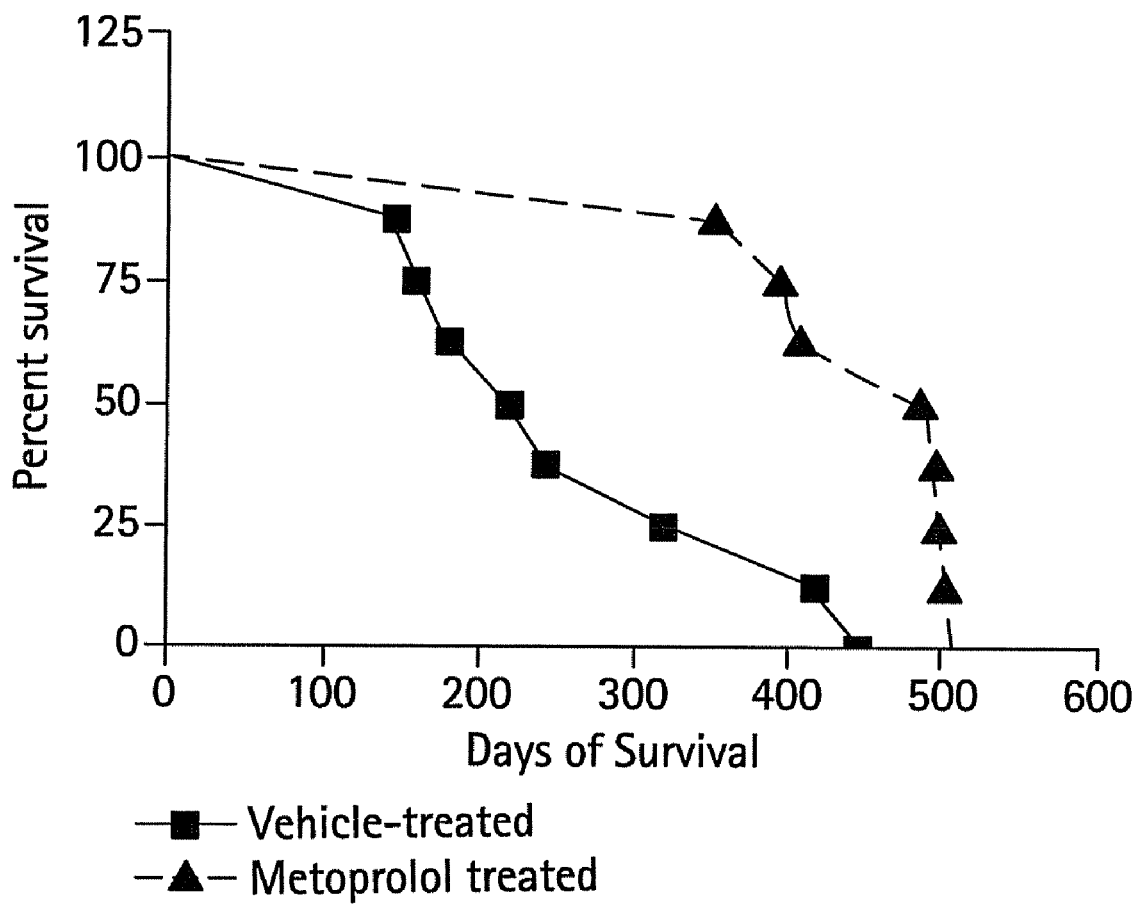
FIG. 29 shows that the combination of MRS2339 and metoprolol, a beta-adrenergic blocker, further enhances survival in P2X$_4$R/CSQ binary mice.

Metoprolol, a beta-adrenergic receptor blocker, was dissolved in drinking water at a concentration of 2 mg/ml. Binary $P2X_4$ receptor/CSQ transgenic mice were fed either regular drinking water (n=8 mice) or drinking water containing the metoprolol (n=8 mice). (FIG. 29) Metoprolol-treated mice showed a median lifespan of 491 days whereas the regular drinking water-treated mice had a median lifespan of 231 days. Log rank test showed the difference in the survival was highly significant with P=0.0028. Because overexpression of the $P2X_4$ receptor rescues calsequestrin mice in a similar manner to MRS2339, administration of a beta blocker such as metoprolol with MRS2339 or another P2X receptor agonist should synergistically increase lifespan.

It has been shown herein that N-methanocarba derivatives of AMP are agonists of P2X receptors, and not P2Y receptors as previously believed. N-methanocarba derivatives of AMP such as MRS2339 are useful in the treatment of cardiac diseases responsive to activation of the cardiac P2X receptor. Cardiac diseases responsive to activation of the cardiac P2X receptors include cardiomyopathy and those diseases associated with defects in cardiac contractility. As agonists of P2X receptors, the N-methanocarba derivatives of AMP are particularly useful in the treatment of cardiac hypertrophy, cardiac failure resulting from abnormal $Ca^{2+}$ homeostasis, for post-myocardial infarction treatment, and post-myocardial infarction treatment within the short-term post-infarction period. The N-methanocarba derivatives of AMP are particularly advantageous because they can enhance cardiac contractile performance, increase survival, work via a cyclicAMP-independent manner.

The terms "a" and "an" do not denote a limitation of quantity, but rather denote the presence of at least one of the referenced items. The term "or" means "and/or". The terms "comprising", "having", "including", and "containing" are to be construed as open-ended terms (i.e., meaning "including, but not limited to"). Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

Chemical compounds are described using standard nomenclature. Unless defined otherwise, all technical and scientific terms used herein have the same meaning as is commonly understood by one of skill in the art to which this invention belongs.

Formula I includes all subformulae thereof. For example Formula I includes compounds of Formulas I and II and the pharmaceutically acceptable salts, prodrugs and other derivatives, hydrates, polymorphs, and thereof.

All forms (for example solvates, optical isomers, enantiomeric forms, polymorphs, free compound and salts) of an active agent may be employed either alone or in combination.

In certain situations, the compounds of Formula I may contain one or more asymmetric elements such as stereogenic centers, including chiral centers, stereogenic axes and the like, e.g. asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with carbon-carbon double bonds may occur in Z- and E-forms, with all isomeric forms of the compounds being included in the present invention. Formula I includes all chiral forms, stereoisomers, diastereomers, and enantiomers of compounds of Formula I.

The term "substituted", as used herein, means that any one or more hydrogens on the designated atom or group is replaced with a selection from the indicated group, provided that the designated atom's normal valence is not exceeded. When the substituent is oxo (i.e., =O), then 2 hydrogens on the atom are replaced. When aromatic moieties are substituted by an oxo group, the aromatic ring is replaced by the corresponding partially unsaturated ring. For example a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent.

A dash ("-") that is not between two letters or symbols is used to indicate a point of attachment for a substituent. For example, —$(CH_2)C_3$-$C_7$cycloalkyl is attached through carbon of the methylene ($CH_2$) group.

"Acyl" is an a group of the formula HC(O)—, alkyl-C(O)— or cycloalkyl-C(O)—, in which alkyl and cycloalkyl carry the definitions set forth in this section. Acyl groups are covalently bound to the parent moiety via a single bond to the carbon of the acyl carbonyl. Non-limiting examples of suitable acyl groups include formyl, acetyl and propanoyl.

"Alkyl" is a branched or straight chain saturated aliphatic hydrocarbon group, having the specified number of carbon atoms, generally from 1 to about 12 carbon atoms. The term $C_1$-$C_4$alkyl as used herein indicates an alkyl group having from 1 to about 4 carbon atoms. Other embodiments include alkyl groups having from 1 to 8 carbon atoms, 1 to 6 carbon atoms or from 1 to 2 carbon atoms, e.g., $C_1$-$C_8$ alkyl, $C_1$-$C_6$ alkyl, and $C_1$-$C_2$ alkyl.

"Alkenyl" is a straight or branched hydrocarbon chain comprising one or more unsaturated carbon-carbon double bonds, which may occur in any stable point along the chain. Alkenyl groups described herein have the indicated number of carbon atoms. $C_2$-$C_6$ alkenyl indicates an alkenyl group of from 2 to about 6 carbon atoms. When no number of carbon atoms is indicated, alkenyl groups described herein typically have from 2 to about 12 carbon atoms, though lower alkenyl groups, having 8 or fewer carbon atoms, are preferred.

Examples of alkenyl groups include ethenyl, propenyl, and butenyl groups.

"Alkynyl" is a straight or branched hydrocarbon chain comprising one or more carbon-carbon triple bonds, which may occur in any stable point along the chain. Alkynyl groups described herein have the indicated number of carbon atoms. $C_2$-$C_6$ alkynyl indicates an alkynyl group of from 2 to about 6 carbon atoms. When no number of carbon atoms is indicated, alkynyl groups described herein typically have from 2 to about 12 carbon "Alkoxy" indicates an alkyl group as defined above with the indicated number of carbon atoms attached through an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. Alkoxy groups include, for example, methoxy groups.

"Alkylthio" indicates an alkyl group as defined above with the indicated number of carbon atoms attached through a sulfhydryl bridge (—SH—). Examples of alkylthio include, but are not limited to, methylthio, ethylthio, and isopropyl thio. Likewise "alkylsulfinyl" is an alkyl group as defined above with the indicated number of carbon atoms attached through a sulfinyl bridge (—S(O)—) via a single covalent bond to the sulfur atom and "alkylsulfonyl" is a group attached through a sulfonyl (—S(O)$_2$—) bridge.

"Aryl" indicates an aromatic group containing only carbon in the aromatic ring or rings. Such aromatic groups may be further substituted with carbon or non-carbon atoms or groups. Typical aryl groups contain 1 or 2 separate, fused, or pendant rings and from 6 to about 12 ring atoms, without heteroatoms as ring members. Such substitution may include fusion to a 5 to 7-membered saturated cyclic group that optionally contains 1 or 2 heteroatoms independently chosen from N, O, and S, to form, for example, a 3,4-methylenedioxy-phenyl group. Aryl groups include, for example, phenyl, naphthyl, including 1-naphthyl and 2-naphthyl, and biphenyl.

In the term "(aryl)alkyl," aryl and alkyl are as defined above, and the point of attachment to the parent moiety is on the alkyl group. Examples of (aryl)alkyl groups include piperonyl and (phenyl)alkyl groups such as benzyl, phenylethyl, and R-phenylisopropyl.

"Arylamino" is an aryl-NH— group. The arylamino group is covalently bound to the parent moiety via a single bond from the nitrogen atom. The nitrogen atom is optionally substituted. "Aryloxy" is an aryl-O— group. The aryloxy group is covalently bound to the parent moiety via a single bond from the oxygen atom. "Arylsulfonyl" is an aryl-S(O$_2$)— group. The bond to the parent moiety is through the sulfonyl.

"Cyano" is the radical —CN.

"Cycloalkyl" indicates saturated hydrocarbon ring groups, having the specified number of carbon atoms, usually from 3 to about 8 ring carbon atoms, or from 3 to about 7 carbon atoms. Examples of cycloalkyl groups include cyclopropyl, cyclobutyl, cyclopentyl, or cyclohexyl as well as bridged or caged saturated ring groups such as norborane or adamantane. A bicyclic cycloalkyl is a saturated bicyclic group having only carbon ring atoms. Bicycloalkyl groups have 7 to 12 carbon ring atoms. Examples of bicycloalkyl groups include s-endonorbornyl and carbamethylcyclopentane.

"Cycloalkoxy" is a cycloalkyl-O—, wherein cycloalkyl is as defined above. Cycloalkoxy groups include cyclopentyloxy.

"Halo" or "halogen" indicates fluoro, chloro, bromo, and iodo.

"Mono- and/or di-alkylamino" indicates secondary or tertiary alkyl amino groups, wherein the alkyl groups are as defined above and have the indicated number of carbon atoms. The point of attachment of the alkylamino group is on the nitrogen. The alkyl groups are independently chosen. Examples of mono- and di-alkylamino groups include ethylamino, dimethylamino, and methyl-propyl-amino. "Mono- and/or dialkylaminoalkyl" groups are mono- and/or di-alkylamino groups attached through an alkyl linker having the specified number of carbon atoms, for example a di-methylaminoethyl group. Tertiary amino substituents may by designated by nomenclature of the form N—R—N—R', indicating that the groups R and R' are both attached to a single nitrogen atom.

A "mono- or bicyclic thiazolyl" group is an optionally substituted thiazolyl, bound via the nitrogen atom or a carbon atom. A bicyclic thiazolyl is a bicyclic heteroaryl group in which the two rings are fused and one ring group is a thiazolyl. The other ring group is a phenyl group or a 5 or 6 membered heteroaryl group having 1 or 2 heteroatoms independently chosen from N, O, and S. The mono- or bicyclic thiazolyl group may be optionally substituted.

"Sulfonyl" is the bivalent radical —SO$_2$—.

"Thiol" is the radical —SH

A suitable "thiazolyl" is (benzothiazolyl)thio-2-propyl.

"Pharmaceutically acceptable salts" includes derivatives of the disclosed compounds in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—(CH$_2$)$_n$—COOH where n is 0-4, and the like. Lists of additional suitable salts may be found, e.g., in *Remington's Pharmaceutical Sciences*, 17th ed., Mack Publishing Company, Easton, Pa., p. 1418 (1985).

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

All cited patents, patent applications, and other references are incorporated herein by reference in their entirety.

The invention claimed is:

1. A method of treating a mammalian subject in need of treatment for a cardiac or vascular disease or condition responsive to activation of the cardiac P2X receptor, comprising administering an effective amount of an N-methanocarba derivative of AMP that activates a cardiac P2X receptor for the treatment of the cardiac or vascular disease or condition responsive to activation of the cardiac P2X receptor, wherein the N-methanocarba derivative of AMP that activates the cardiac P2X receptor is of the formula:

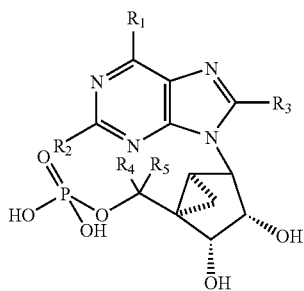

or a pharmaceutically acceptable salt thereof, wherein:

$R_1$ is hydrogen, alkyl, alkoxy, amino, mono- or di-alkylamino, mono or bicyclic cycloalkyl, cycloalkyloxy, aryl, arylalkyl, acyl, sulfonyl, arylsulfonyl, or a mono- or bicyclic thiazolyl group; and $R_2$ is hydrogen, halogen, thiol, cyano, alkyl, alkenyl, alkynyl, alkylthio, alkylsulfinyl, alkylsulfonyl, aryl, arylamino, or aryloxy;

$R_3$ is hydrogen, halogen, methyl, or ethyl; and $R_4$ and $R_5$ are independently hydrogen, methyl, or methoxy, wherein the cardiac or vascular disease or condition responsive to activation of the cardiac P2X receptor is a post-myocardial infarction condition, or diastolic heart failure.

2. The method of claim 1, wherein $R_1$ is hydrogen, $C_1$-$C_4$alkyl, $C_1$-$C_4$alkoxy, amino, mono- or di-$C_1$-$C_4$alkylamino, $C_3$-$C_7$cycloalkyl, or $C_3$-$C_7$cycloalkyloxy;

$R_2$ is hydrogen, halogen, thiol, cyano, $C_1$-$C_4$alkyl, $C_1$-$C_4$alkylthio, $C_1$-$C_4$alkylsulfinyl, or $C_1$-$C_4$alkylsulfonyl; and $R_3$, $R_4$, and $R_5$ are all hydrogen.

3. The method of claim 1, wherein $R_1$ is $NH_2$ or $CH_3NH$;

$R_2$ is H, Cl, $SCH_3$ or $SOCH_3$; and $R_3$, $R_4$, and $R_5$ are all hydrogen.

4. The method of claim 1, wherein the N-methanocarba derivative of AMP is

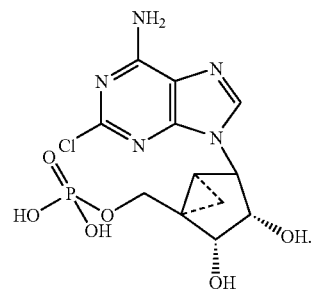 [SMILES: Nc1nc(Cl)nc2c1ncn2C1[C@H]2C[C@@]2(COP(=O)(O)O)[C@@H](O)[C@H]1O]

5. The method of claim 1, wherein the post-myocardial infarction condition is post-myocardial infarction conditions within the short-term post-infarction period.

6. The method of claim 1, further comprising administering a beta-adrenergic blocker, an angiotension receptor blocker, or an angiotensin converting enzyme blocker.

7. The method of claim 1, wherein the post-myocardial infarction condition is ischemic cardiomyopathy.

8. A method of improving cardiac contractile performance in a mammal in need thereof, comprising administering an effective amount of an N-methanocarba derivative of AMP that activates a cardiac P2X receptor for improving cardiac contractile performance, wherein the N-methanocarba derivative of AMP that activates a cardiac P2X receptor is of the formula:

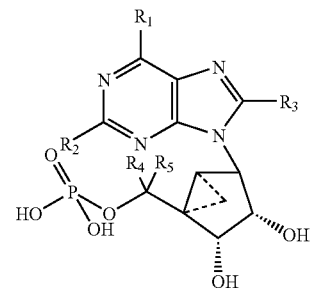

or a pharmaceutically acceptable salt thereof, wherein:

$R_1$ is hydrogen, alkyl, alkoxy, amino, mono- or di-alkylamino, mono or bicyclic cycloalkyl, cycloalkyloxy, aryl, arylalkyl, acyl, sulfonyl, arylsulfonyl, or a mono- or bicyclic thiazolyl group; and $R_2$ is hydrogen, halogen, thiol, cyano, alkyl, alkenyl, alkynyl, alkylthio, alkylsulfinyl, alkylsulfonyl, aryl, arylamino, or aryloxy;

$R_3$ is hydrogen, halogen, methyl, or ethyl; and $R_4$ and $R_5$ are independently hydrogen, methyl, or methoxy, wherein the mammal has had a myocardial infarction, or wherein the mammal is in need of treatment for diastolic heart failure.

9. The method of claim 8, wherein $R_1$ is hydrogen, $C_1$-$C_4$alkyl, $C_1$-$C_4$alkoxy, amino, mono- or di-$C_1$-$C_4$alkylamino, $C_3$-$C_7$cycloalkyl, or $C_3$-$C_7$cycloalkyloxy;

$R_2$ is hydrogen, halogen, thiol, cyano, $C_1$-$C_4$alkyl, $C_1$-$C_4$alkylthio, $C_1$-$C_4$alkylsulfinyl, or $C_1$-$C_4$alkylsulfonyl; and $R_3$, $R_4$, and $R_5$ are all hydrogen.

10. The method of claim 8, wherein administering is performed within the short-term post-infarction period.

11. The method of claim 8, wherein the N-methanocarba derivative of AMP is a compound of the formula:

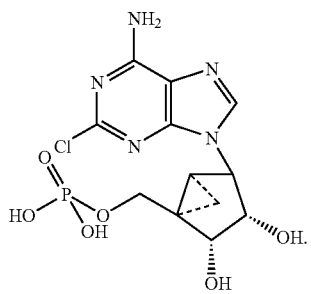 [SMILES: Nc1nc(Cl)nc2c1ncn2C1[C@H]2C[C@@]2(COP(=O)(O)O)[C@@H](O)[C@H]1O]

12. The method of claim 8, wherein the post-myocardial infarction condition is ischemic cardiomyopathy.

13. A method of treating a mammalian subject in need of treatment for a cardiac hypertrophy, comprising
administering an effective amount of a cardiac P2X receptor agonist,
wherein the N-methanocarba derivative of AMP is a compound of the formula:

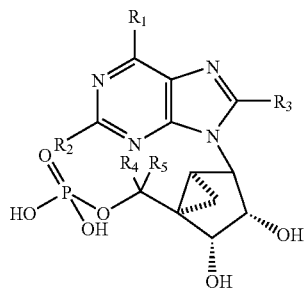

or a pharmaceutically acceptable salt thereof, wherein:

$R_1$ is hydrogen, alkyl, alkoxy, amino, mono- or di-alkylamino, mono or bicyclic cycloalkyl, cycloalkyloxy, aryl, arylalkyl, acyl, sulfonyl, arylsulfonyl, or a mono- or bicyclic thiazolyl group; and $R_2$ is hydrogen, halogen, thiol, cyano, alkyl, alkenyl, alkynyl, alkylthio, alkylsulfinyl, alkylsulfonyl, aryl, arylamino, or aryloxy;

$R_3$ is hydrogen, halogen, methyl, or ethyl; and $R_4$ and $R_5$ are independently hydrogen, methyl, or methoxy.

14. The method of claim 13, wherein the N-methanocarba derivative of AMP is a compound of the formula:

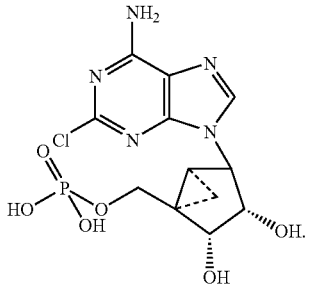 [SMILES: Nc1nc(Cl)nc2c1ncn2C1[C@H]2C[C@@]2(COP(=O)(O)O)[C@@H](O)[C@H]1O]

* * * * *